(12) United States Patent
Davis et al.

(10) Patent No.: US 9,867,847 B2
(45) Date of Patent: Jan. 16, 2018

(54) ABSORBENT INGESTIBLE AGENTS AND ASSOCIATED METHODS OF MANUFACTURE AND USE

(71) Applicant: WELLOSOPHY CORPORATION, Clearwater, FL (US)

(72) Inventors: Richard Davis, Clearwater, FL (US); Lior Sher, Clearwater, FL (US)

(73) Assignee: Wellosophy Corporation, Clearwater, FL (US)

( * ) Notice: Subject to any disclaimer, the term of this patent is extended or adjusted under 35 U.S.C. 154(b) by 0 days.

(21) Appl. No.: 15/243,195

(22) Filed: Aug. 22, 2016

(65) Prior Publication Data

US 2016/0361351 A1 Dec. 15, 2016

Related U.S. Application Data

(62) Division of application No. 12/365,447, filed on Feb. 4, 2009, now Pat. No. 9,457,048.

(60) Provisional application No. 61/059,420, filed on Jun. 6, 2008, provisional application No. 61/026,183, filed on Feb. 5, 2008.

(51) Int. Cl.

| | |
|---|---|
| *A61K 31/78* | (2006.01) |
| *A61K 9/00* | (2006.01) |
| *A61K 9/48* | (2006.01) |
| *A61K 31/198* | (2006.01) |
| *A61K 31/201* | (2006.01) |
| *A61K 33/06* | (2006.01) |
| *A61K 45/06* | (2006.01) |
| *A23L 33/00* | (2016.01) |
| *A23L 33/175* | (2016.01) |
| *A23L 33/25* | (2016.01) |
| *A61K 47/18* | (2017.01) |
| *C08F 120/06* | (2006.01) |

(52) U.S. Cl.
CPC ............ *A61K 31/78* (2013.01); *A23L 33/175* (2016.08); *A23L 33/25* (2016.08); *A23L 33/30* (2016.08); *A61K 9/0053* (2013.01); *A61K 9/0056* (2013.01); *A61K 9/0065* (2013.01); *A61K 9/485* (2013.01); *A61K 9/4858* (2013.01); *A61K 9/4866* (2013.01); *A61K 31/198* (2013.01); *A61K 31/201* (2013.01); *A61K 33/06* (2013.01); *A61K 45/06* (2013.01); *A61K 47/183* (2013.01); *C08F 120/06* (2013.01); *A23V 2002/00* (2013.01); *C08F 2810/20* (2013.01)

(58) Field of Classification Search
CPC ......... A61K 9/0053; A61K 9/48; A61K 31/78
See application file for complete search history.

(56) References Cited

U.S. PATENT DOCUMENTS

| | | |
|---|---|---|
| 2,649,439 A | 8/1953 | Brown |
| 4,340,706 A | 7/1982 | Obayashi |
| 4,518,768 A | 5/1985 | Scheurer |
| 4,654,039 A | 3/1987 | Brandt |
| 4,666,983 A | 5/1987 | Tsubakimoto |
| 4,734,478 A | 3/1988 | Tsubakimoto |
| RE32,649 E | 4/1988 | Brandt |
| 4,797,282 A | 1/1989 | Wahlig |
| 4,968,508 A | 11/1990 | Oren |
| 5,093,472 A | 3/1992 | Bresciani |
| 5,145,906 A | 9/1992 | Chambers |
| 5,336,486 A | 8/1994 | Acharya |
| 5,506,324 A | 4/1996 | Gartner |
| 5,629,377 A | 5/1997 | Burgert |
| 5,750,585 A | 5/1998 | Park |
| 6,159,591 A | 12/2000 | Beihoffer et al. |
| 6,271,278 B1 | 8/2001 | Park |
| 6,914,099 B2 | 7/2005 | Kim |
| 2003/0211071 A1 | 11/2003 | Bologna |
| 2004/0180088 A1 | 9/2004 | Dudhara et al. |
| 2004/0192582 A1 | 9/2004 | Burnett et al. |
| 2004/0236049 A1 | 11/2004 | Fuchs et al. |
| 2006/0141039 A1 | 6/2006 | Boyd |
| 2008/0045916 A1 | 2/2008 | Herfert et al. |
| 2009/0324537 A1 | 12/2009 | Bucevschi et al. |
| 2010/0215732 A1 | 8/2010 | Mintchev et al. |

FOREIGN PATENT DOCUMENTS

| | | |
|---|---|---|
| EA | 007247 B1 | 8/2003 |
| GB | 2119384 | 11/1983 |
| JP | H02-503205 A | 10/1990 |
| JP | H05-23136 A | 2/1993 |
| JP | H06-056931 A | 3/1994 |

(Continued)

OTHER PUBLICATIONS

Chemical Abstracts, vol. 111, No. 18, Oct. 30, 1989, Columbus, Ohio; abstract No. 155076, Manufacture of Water-Absorbents Containing Low Residual Monomers, p. 50, col. 2 & JP-A-01 103 644 (Sanyo Chem. Ind. Ltd.).

Chen J et al., Gastric retention properties of superporous hydrogel composites. Journal of Controlled Release, Elsevier, Amsterdam, NL, vol. 64, No. 1-3, 2000, pp. 39-51.

Omidian H et al. Advances in Superporous hydrogels. Journal of Controlled Release. 2005. 102(1): 3-12. XP027664513.

Omidian H et al. Recent developments in superporous hydrogels. Journal of Pharmacy and Pharmacology. 2007. 59(3): 317-327. XP055168354.

(Continued)

*Primary Examiner* — Alma Pipic

(74) *Attorney, Agent, or Firm* — Bryan D. Zerhusen; Locke Lord LLP

(57) ABSTRACT

Appetite suppression and weight management achieved through pre-meal ingestion of temporary gastric bulking agents in the form of superabsorbent polymer hydrogels (SAPHs) selected from among a group consisting of cross-linked polycarboxylic acid moieties is described. The preferred compositions and manufacturing methods of ultra-pure preparations of ingestible forms; as well as the preferred methods of use, dosage and administration; distribution and delivery of SAPH materials are also described.

10 Claims, 3 Drawing Sheets

(56) References Cited

FOREIGN PATENT DOCUMENTS

| JP | 2002-501563 A | 1/2002 |
| JP | 2002-360222 A | 12/2002 |
| JP | 2004-538301 A | 2/2004 |
| RU | 2286801 C2 | 11/2006 |
| WO | WO 92/20723 | 11/1992 |
| WO | WO 2004/056343 A1 | 7/2004 |
| WO | WO 2007/112436 A2 | 10/2007 |
| WO | WO 2007/115169 A2 | 10/2007 |

OTHER PUBLICATIONS

Wellosophy Corporation PREE™, www.wellosophcorp.com, Jul. 29, 2008, XP055168936, Retrieved from the Internet: URL:http://web.archive.org/web/20080729155001/http://www.wellosophycorp.com/pree.asp.
Wichterle et al., Hydrophilic gels for biological use, Nature, 185: 117-118, 1960.
Yukio Mizutani. Superabsorbent poly(acrylic acid) complex. Journal of Applied polymer Science, vol. 61, No. 5, Aug. 1, 1996, pp. 735-739, XP055168628.
International Search Report dated Jul. 31, 2009, for PCT/US2009/033157.
Supplementary Partial European Search Report dated Feb. 11, 2015, and issued Feb. 19, 2015, for EP20090708495.
Supplementary European Search Report dated Feb. 11, 2015, and issued Jul. 12, 2015, for EP 20090708495.
D.Ju.Salepugin and all, Poluchenie poristykh biorezorbiruemykx polimerov obrabotkoi dioksidom ugleroda v gazoobraznom, shidkom I sverkhkriticheskom sostoyaniyakh. "Sverkhkriticheskie fljuidy: teoriya I praktika" 2007 v.2 No. 1, p. 61-68 (Foiniation of Porosity in Bioresorbable Polymers by their Treatment in Gaseous, Liquid and Supercritical Carbon Dioxide).
Badiger et al., Porogens in the preparation of microporous hydrogels based on poly (ethylene oxides), Biomaterials, 14: 1059-1063, 1993.
Barvic et al., Biologic properties and possible uses of polymer-like sponges, J. Biomed. Mater. Res., 1: 313-323, 1967.
C.J. Benning, Plastic Foams: the physics and chemistry of product performance and process technology. vol. 1, Polymer Engineering & Technology, (1969) Chptrs. 6, 7, 9, 10, 14. Wiley-Interscience.
F. Rodriguez, Principles of Polymer Systems. 2.sup.nd ed. (1982) pp. 363-378, Hemisphere Publ. Corp.
F.A. Shutov, Integral/Structural Polymer Foams: Technology, Properties and Applications. (1986) Chptrs. 1, 21. Springer Verlag.
Holly et al., Water wettability of hydrogels, in Hydrogels for Medical and Related Applications, American Chemical Society, Washington, DC, 1976, 252-266.
Park, K. "Enzyme-digestible swelling hydrogels as platforms for long-term oral drug delivery: synthesis and characterization", Biomaterials (Sep. 1988), pp. 435-441, vol. 9, Butterworth & Co.
Kabra et al., Rate-limiting steps for solvent sorption and desorption by microporous stimuli-sensitive absorbent gels, in Superabsorbent Polymers, American Chemical Society, Washington, DC, 1994, 76-86.
Park et al., Honey, I blew up the hydrogels!, Pro. Intern. Symp. Control. Rel. Bioact. Mater., 21: 21-22, 1994.
Park et al., Hydrogel foams: A new type of fast swelling hydrogels, The 20th Annual Meeting of the Society for Biomaterials, Abstract #158, 1994.
Ratner, B. D., Hydrogel surfaces, in Hydrogels in Medicine and Pharmacy. vol. I. Fundamentals, CRC Press, Inc., Boca Raton, FL, 1986, 85-94.
Shalaby et al., In vitro and in vivo studies of enzyme-digestible hydrogels for oral drug delivery, J. Controlled. Rel., 19: 131-144, 1992A.
Shalaby et al., Use of ultrasound imaging and fluoroscopic imaging to study gastric retention of enzyme-digestible hydrogels, Biomaterials, 13:289-296, 1992.
Tanaka et al., Kinetics of swelling of gels, J. Chem. Phys., 70: 1214-1218, 1979.
1990 U.S. Pharmacopeia National Formulary U.S.P. XXII, NF XVII, pp. 1910-1912.
PREE® FAQ's, http://www.wellosophy.com/preefaqs.htm, accessed on Aug. 12, 2015, pp. 1-4.
"Understanding Mesh Sizes" (http://www.espimetals.com/index.php/faq/334-understanding-mesh-sizes, Accessed on Aug. 29, 2015, pp. 1-2).
Excipient definition (https://www.wordnik.com/words/excipient, Accessed on Mar. 6, 2015, 1 page).
Mizutani (Journal of Applied Polymer Science, vol. 61, pp. 735-739, Published 1996).
Kiatkamjornwong et al. (Journal of Applied Polymer Science, vol. 72, pp. 1349-1366, Published 1999).

US 9,867,847 B2

ABSORBENT INGESTIBLE AGENTS AND ASSOCIATED METHODS OF MANUFACTURE AND USE

CROSS-REFERENCE TO RELATED APPLICATIONS

Under 35 U.S.C. §119(e) this application claims the benefit of U.S. application Ser. No. 12/365,447, filed on Feb. 4, 2009; titled: Absorbent Ingestible Agents and Associated Methods of Manufacture and Use; and U.S. Provisional Application Ser. No. 61/026,183 filed Feb. 5, 2008; entitled: Polymeric Agents and Associated Methods of Use for Appetite Suppression and Weight Management; and U.S. Provisional Patent Application Ser. No. 61/059,420 filed Jun. 6, 2008; entitled: Ingestible SAPH Mixtures with Improved Water-Swelling Characteristics; the disclosures of which are hereby incorporated by reference in their entirety.

FIELD OF THE INVENTION

This invention relates to compositions and methods of administering ingestible forms of absorbent polycarboxylic acid polymers capable of absorbing large amounts of water in the gastric environment and which are well suited for use as temporary pre-meal gastric bulking agents designed to maximally suppress appetite thus assisting in both short-term weight loss as well as long-term weight management.

BACKGROUND

Widespread obesity and excessive weight gain have become widely recognized as an emerging global pandemic. Data recently published by the World Health Organization estimates that in 2007, 1.6 billion people (one in four) were overweight or obese. Four hundred million of these were children. Modern societies are being crippled with the associated costs of overburdened healthcare systems that are crumbling beneath the weight of out-of-control medical costs associated with managing the numerous life-threatening and often fatal diseases associated with excessive weight. Type 2 diabetes, certain cancers, stroke, hypertension, age-related eye diseases, along with heart, liver and kidney disease are significantly prevalent co-morbid conditions that plague this population.

Weight management was once considered only an issue of vanity. Now it has escalated into a health crisis of unprecedented proportion. Currently, thousands of products and technologies have been commercialized to assist overweight and obese people in their goal to lose and manage their weight. However, the issue of residual post-prandial hunger remains an unsolved and fundamental issue for most calorie-restricted diets and weight loss plans. Despite the best of intentions, the "battle of the bulge" is rarely won. The seeds of defeat lay in the fact that weight control is regulated by numerous redundant hormonal systems that are dedicated to preserving weight. In addition, calorie restriction in human physiology causes the generation of "hunger" pains, headaches, nausea and other deprivation sensations which are often so severe that it becomes nearly impossible for most dieting persons to control their urge to eat through the sheer exercise of their willpower alone.

Although numerous attempts have been made to promote a feeling of "fullness" or satiety, when the stomach is not in fact filled with food, each proposed means has encountered difficulties in achieving a desired level of practical success. High fiber diets require the consumption of substantial volumes of material leading to large increases in flatulence, abdominal discomfort and increased elimination volumes. Central nervous system stimulants have severe and occasionally fatal side effects. Thickening agents and rheological modifiers have minimal efficacy. Surgical procedures, while often effective, are risky and very expensive.

Therefore, there exists in the art an ongoing need for safe and effective compositions and methods that allow individuals to reduce caloric intake to lose weight while also minimizing the residual hunger which leads to a relapse of overeating. The present invention seeks to address one or more of these needs in the art.

SUMMARY

This invention relates to the field of hunger management, particularly to ingestible compositions and methods for weight-loss and weight management. In certain aspects the invention encompasses ultrapure bio-inert super-absorbent polymer hydrogel (SAPH) or gastric bulking agent compositions that once ingested, aid in temporarily suppressing appetite and/or promoting a feeling of early satiety by mechanically occupying gastric volume and or modifying the hormonal milieu that controls satiety in persons seeking to reduce their caloric intake by downsizing their meal portion sizes with a reduced or absent feeling of residual hunger.

In another aspect, the invention encompasses methods for controlling appetite comprising administering to an individual or consuming an effective amount of an ingestible super-absorbent polycarboxylic acid polymer, wherein the polymer absorbs water in the gastric environment. In certain aspects the methods include administering a SAPH or bulking composition of the invention as a temporary pre-meal gastric bulking agent to suppress appetite, and therefore, assist in weight management and/or promote a feeling of early satiety in an individual. In still other aspects the invention relates to methods for reducing caloric intake in an individual comprising administering to an individual or consuming an effective amount of the polycarboxylate composition of the invention.

In any of the aspects or embodiments described herein, an effective amount of the SAPH or bulking composition of the invention may be provided as food additive or dietary supplement composition, which may be administered or ingested at least once daily in unitary dosage form, and in any pharmaceutically acceptable dosage form known or which becomes known by those of skill in the art. In addition, the dietary supplement can be administered by any pharmaceutically acceptable route recognized by those of skill in the art, for example, oral, enteral, parenteral, intravenous, transdermal, nasal, rectal, topical, vaginal or the like. In a preferred embodiment, the dietary supplement of the invention is a unitary dosage form suited for oral administration or consumption by an individual at least once per day, for example, in a capsule, tablet, caplet, soft gel capsule, controlled release tablet, powder, liquid, liquid or gel filled capsule, and the like.

Additional aspects and advantages of the SAPH compositions which are encompassed by the invention will become evident from the description, non-limiting examples, and claims that follow.

DETAILED DESCRIPTION

Figure 1:
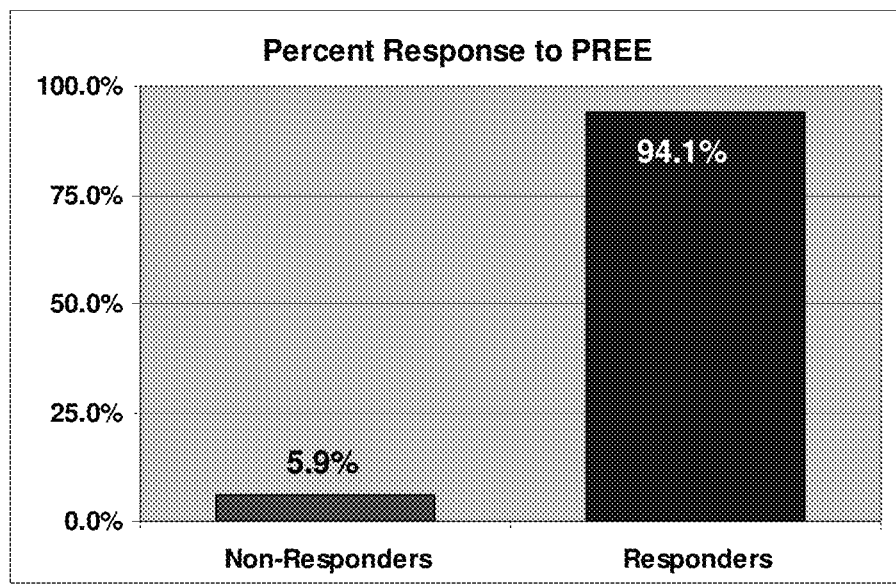
FIG. 1. Graphical representation of clinical trial data relating to participant response to ingestion of an exemplary SAPH composition of the invention (commercially available as PREE™). Participants were asked to rate their responses to PREE™ at each of breakfast, lunch and dinner.

The present invention relates to the discovery of surprising and unexpected swelling characteristics of the SAPH compositions of the invention. As such, the SAPH compositions of the invention are advantageous and efficacious as dietary supplements or weight loss/weight management compositions. In particular, the compositions described herein allow for the surprising and unexpectedly beneficial gastric swelling characteristics making them useful as food additives or dietary supplements for the control of food portions, attenuating hunger, and promoting weight loss and/or facilitating weight management.

As used herein, the terms "super-absorbent polymer hydrogel," "polymer hydrogel," "SAPH," "SAPH material," "SAPH composition," "absorbent ingestible agent," "bulking composition," and "gastric bulking agent", and combinations thereof, are used interchangeably in reference to compositions and methods of the invention.

Physiologic control over eating and weight maintenance is highly redundant. In fact, numerous complex signaling pathways have been evolutionarily conserved to protect the human body against weight change—especially weight loss. These compensatory mechanisms are interactive and overlapping. As a result, dietary and medical methods designed to achieve weight loss have historically delivered poor results, and even when temporally successful, are difficult to sustain. As such, described herein are compositions and methods useful for regulating and/or suppressing the appetite in an individual. In certain methods of the invention, compositions of the invention are administered to or ingested by an individual in unitary dosage form for the reduction of body mass; i.e., body weight.

This application claims the benefit of U.S. Provisional Application Ser. No. 61/026,183 filed Feb. 5, 2008; and U.S. Provisional Patent Application Ser. No. 61/059,420 filed Jun. 6, 2008; the disclosures of which are hereby incorporated by reference in their entirety.

Several peripheral signaling pathways are known to regulate energy homeostasis (See Table 1). Insulin and leptin are hormones that circulate in proportion to body fat mass and act upon receptors within the hypothalamus to reduce appetite. When body fat mass is reduced during weight loss, insulin and leptin levels decline, strongly stimulating appetite and weight gain. Another controlling hormone, ghrelin, is produced primarily by the gastric epithelium, and appears to stimulate appetite and feeding. Ghrelin levels are inversely related to body weight, with obese people displaying low ghrelin levels. Diet-induced weight loss has been shown to increase ghrelin levels, implying that ghrelin may play a role in countering such weight loss by stimulating appetite and energy intake.

Ghrelin and is primarily found in the epithelial cells of the stomach, but also in various areas of the brain and hypothalamus. Before eating the levels of ghrelin are very high, which stimulates brain cells telling us that we should eat. After eating, the levels of this hormone decrease considerably. One of the hormones that counteract the effects of ghrelin is leptin. Leptin is released by adipose tissue and serves as is the "satiety hormone," since it provides the hypothalamic neuronal cells with satiation signals. At elevated plasma levels, leptin induces a sense of satiety, even several hours after food consumption.

Like leptin, the appetite-blocking hormone called obestatin, produced by the same epithelial cells as ghrelin, also down-regulates hunger. As obestatin levels increase, receptor signaling to the brain's satiety center is also increased thus reducing hunger sensation. In addition, food intake is regulated by additional CNS receptors, including the melanocortin and neuropeptide Y (NPY) systems in the arcuate nucleus. The NPY Y2 receptor (Y2R), a putative inhibitory presynaptic receptor, is highly expressed on NPY neurons in the arcuate nucleus, which is accessible to peripheral hormones. Peptide YY(3-36) (PYY(3-36)), a Y2R agonist, is released from the gastrointestinal tract postprandially (i.e., after eating a meal) in proportion to the calorie content of a meal which suppresses appetite.

TABLE 1

Summary of Appetite Modifying Hormones

| Circulating Hormone | Primary Action | Where Produced |
| --- | --- | --- |
| Leptin | Appetite Suppressant | Adipose Tissue |
| Ghrelin | Appetite Stimulant | Gastric Epithelium |
| Obestatin | Appetite Suppressant | Gastric Epithelium |
| PYY(3-36) | Y2R Agonist, Appetite Suppressant | Gastric Epithelium |

Historically, ingestible crosslinked polycarboxylic acids have enjoyed a wide variety of uses, for example, in the pharmaceutical, food contact and cosmetics industries. However, prior polyacrylates only achieve small swelling ratios. However, a successful gastric bulking agent will need to exhibit substantially higher swelling ratios that can occur within the gastric environment, preferably at least in excess of 200 times gram for gram of water absorption, more preferably at least in excess of 350 times gram for gram of water absorption, and most preferably at least in excess of 500 times gram for gram of water absorption.

Adapting a synthetic SAPH material for use as a gastric bulking agent requires overcoming a number of problems known in the art, including: a) identifying a unified and commercially reasonable combination of an appropriate composition of matter; b) a simple and cost-effective method of manufacture that will meet regulatory requirements for ingestible purposes; c) correct routes of administration; d) ideal delivery methods, and e) proper dosing regimens, as such are all disclosed in the present invention.

Currently available bulking agents, for example, calcium polycarbophil, have proven unsuitable for the present use, i.e., weight loss/appetite control, because the end products swell too little or too slowly to be acceptable as pre-meal gastric bulking agents that are designed to be taken with water prior to meals. For this reason, these materials are currently commercialized in ingestible forms as bulk laxatives and have the laxative effect, which is clearly not considered a desirable side effect of the intended purpose of the present invention. Moreover, the calcium polycarbophil agents have a mild muco-adhesive tendency which potentially could interfere with the concomitant ingestion of other foods, nutrients, medicants or other products that would reasonably be consumed by overweight users of the present invention seeking to lose or manage their weight.

Other issues that have been encountered with prior bulking agents include the excessive presence of undesirable, toxic or carcinogenic by-products or contaminants in SAPH materials which occur during their manufacture, i.e., residual solvents (Scheurer focused exclusively on benzene removal), and by further mention—residual monomers, or residual low molecular weight oligomers, or residual heavy metals which would make such a material entirely unsuited for the intended use as an ingestible product. Furthermore, excess concentrations of unwanted contaminants are even less desirable due to the relatively large volumes of SAPH materials needed to be ingested to provide for an effective temporary pre-meal gastric bulking agent indication.

The present invention offers a number of surprising and unexpected advantages over the currently known bulking agents. For example, ingestible material must continuously meet stringent regulatory requirements with respect to toxicity, safety, carcinogenicity, manufacturability, purity and environmental standards. In addition, the SAPH material must be approvable by regulatory authorities for use as a gastric bulking agent used as a weight loss/weight management tool. With respect to the manufacture of hydrogels in general and to SAPH compositions of the present invention, the selection of: a) raw materials for polymerization and cross-linking; b) solvents, and c) manufacturing agents and methods must each be chosen with the end product use as an ingestible agent in mind—as has been accomplished by the present invention. Typically, additional or secondary operations must be performed to remove each one of the three classes of unwanted contaminants in the desired final product: a) residual monomer and low molecular weight oligomers; b) residual solvent, or c) residual heavy metal contaminants. However, the invention encompasses a single, unified methodology that encompasses the simultaneous removal of all three forms of undesired impurities to levels sufficiently reduced to meet regulatory scrutiny and thus commercial viability.

Also, the SAPH material must be provided in a conveniently ingestible form for the stated purpose; i.e. ideally fast-dissolving capsules or gel caps when used as an uncombined weight loss or weight management tool with a rapidly absorbing SAPH that will adsorb the free water concurrently ingested with the capsules or gel caps. Rapid capsule dissolution and SAPH absorption is necessary so that the free water is absorbed in the stomach by the SAPH prior to its gastric absorption or transport into the small intestine where it loses its effectiveness for the purposes of the present invention.

Next, in order to be effective for hunger control/weight management, the SAPH material should provide sufficient volumetric bulking to promote a sense of early satiety. In certain embodiments, the volumetric bulking of the SAPH composition of the invention is at least in excess of 200 times gram for gram of water absorption; at least in excess of 350 times gram for gram of water absorption; or at least in excess of 500 times gram for gram of water absorption.

In certain embodiments, the SAPH or bulking compositions of the invention have an average pre-swell particle or grain size of from about 100 nm to about 1 mm. The inclusion of some micronized or "fines" of the SAPH materials into a dietary supplement/weight management composition has unexpectedly been found to be advantageous for enhancing at least one of the volumetric bulking and/or rate of swelling. The amount of fines, however, must be carefully controlled to avoid unwanted oncotic effects. In other words, if the weight percentage of the fines is too high, a bulk laxative effect may ensue due to the net water inflow into the gut. Therefore, in certain embodiments, the SAPH or bulking compositions of the invention comprise from about 0.5% to about 25% by weight of fines. In any of the embodiments described herein the fines may have an average pre-swell particle or grain size of from about 0.5 microns to about 50 microns. In certain additional embodiments, the SAPH composition comprises from about 1% to about 5% by weight of fines. In any of the embodiments described herein, the fines may have an average grain size of from about 1 micron to about 25 microns. In still further embodiments, the SAPH compositions of the invention comprise polymer particles or grains having a plurality of average pre-swell grain sizes. The particular particle size number and distribution will be selected depending on a number of considerations including desired volumetric bulking, swelling rate, and/or unitary dosage size. Particles or gains can be separated on mesh screens of any desired pore size, for example, 1 mm, 900 micron, 800 micron, 700 micron, 600 micron, 500 micron, 400 micron, 300 micron, 200 micron, 100 micron or less. All mesh sizes occurring in between the exemplified sizes are expressly contemplated. In certain embodiments the SAPH material of the invention comprises (by weight of total amount of SAPH material) from about 0% to about 5% of particles separated on a 850 micron mesh; from about 5% to about 20% of particles separated on a 500 micron mesh; from about 25% to about 90% of particles separated on a 180 micron mesh; and from about 1% to about 15% of particles separated on a 106 micron mesh; and from about 0.5% to about 5% of fines having an average size of between about 1 micron and 25 microns.

Also, in order to be effective for hunger control/weight management, the SAPH material must be able to provide its action in the gastric environment consisting of a unique and widely variable pH, and salinity ranges at physiologic temperature. In addition, the SAPH material must be non-digestible, so that the hydrogel remains bio-inert throughout its transit in the body's gastrointestinal tract. Similarly, the body will need to recognize the SAPH as a particulate in order for the material to be retained in the gastric lumen for a time that is sufficient for the purposes of an effective temporary pre-meal gastric bulking agent. The above-features are met by one or more embodiments of the SAPH composition of the present invention. In certain embodiments, the SAPH composition of the invention demonstrates an average swollen particle size of from about 0.5 mm to 2 mm in the final water-swollen form of the SAPH.

In one or more embodiments of the SAPH composition of the invention, the SAPH material is a water retentive polyelectrolyte hydrogel, not merely a hydrogel sponge, such that the absorbed water will not be released during gastrointestinal transit; neither is it absorbable nor will it absorb other materials from the gastrointestinal (GI) tract; is tough enough to withstand peristaltic action to remain in a large particle size to prevent oncotic pressure changes during transit; is able to be eliminated from the GI tract without difficulty and cannot adhere to oral or gastrointestinal linings; is bio-compatible or more preferably bio-inert and remains such during GI transit.

Additional advantages offered by the present invention include one or more of a) is not an ecological or environmental hazard; b) is manufacturable at a low cost and easily flowable; especially into encapsulation embodiments where the potential for degradation or oxidation by other excipients over the course of the product's shelf life must be minimized; c) is fast acting, and d) offers a convenient and non-invasive mechanism of action.

Therefore, in one aspect the invention relates to compositions that produce or simulate pre-meal gastric volume in order to promote a pre-synaptic mechanical stimulus to gastric receptors. Consumption of the compositions of the invention elicit natural physiologic responses which govern the release of one or more of these hormonal mediators, timed to decrease the urge to eat and curb the feelings of hunger just prior to, or just upon the initiation of eating. In another aspect, the invention relates to compositions that, when used regularly over time, induces a progressive physiological modification within these complex signaling pathways. The result is a modification or override of the normal energy-management homeostatic responses of the body over time in order to achieve a sustained state of weight reduction by resetting the "satiety threshold" governed by central nervous system receptors responsive to circulating hormones released by gastric sensory mechanisms.

In certain aspects, the SAPH materials of the invention comprise one or more hydrogel forming polycarboxylic acid compounds formulated for oral administration to or ingestion by an individual. In any of the SAPH or gastric bulking compositions described herein, the composition can comprise from about 1% to about 99% by weight of a crosslinked polycarboxylic acid. In additional embodiments, the gastric bulking composition comprises from about 10%, or 20%, or 30%, or 40%, or 50% to about 99% by weight of a crosslinked polycarboxylic acid. The invention includes all amounts between the identified ranges. In another embodiment, the SAPH material or bulking agent comprises at least one of a crosslinked homopolymer of polyacrylic acid or polyacrylamide; a crosslinked copolymer of polyacrylic acid and polyacrylamide; the alkali metal salts of these materials or a combination thereof.

In any of the embodiments described herein, the polymers of the SAPH material can be prepared from one or more ethylenically unsaturated carboxylic acids; ethylenically unsaturated carboxylic acid anhydrides, or acid or basic salts thereof. Additionally, the polymers may include comonomers, which are known in the art, for grafting onto the SAPH materials including comonomers such as an acrylamide, an acrylonitrile, a vinyl pyrrolidone, a vinyl sulphonic acid or a salt thereof, a cellulosic monomer, a modified cellulosic monomer, a polyvinyl alcohol or a starch hydrolyzate. In certain embodiments the SAPH material of the invention includes a comonomer comprising greater than about 5 percent by weigh of the monomer mixture. In other embodiments, the SAPH material includes a comonomer comprising greater than about 10 percent by weight of the monomer mixture. In other embodiments, the SAPH material of the invention includes a comonomer comprising about 25 percent by weight of the monomer mixture.

In any of the embodiments described herein, the unsaturated carboxylic acid and carboxylic acid anhydride monomers may include at least one of an acrylic acid such as, for example, but without limitation, acrylic acid, methacrylic acid and ethacrylic acid. In other embodiments, grafted or copolymer examples may include the use of acrylamide, an acrylonitrile, a vinyl pyrrolidone, a vinyl sulphonic acid or a salt thereof, a cellulosic monomer, a modified cellulosic monomer, a polyvinyl alcohol or a starch hydrolyzate can be selected. In an embodiment, the starting monomer is acrylic acid, methacrylic acid, or a salt thereof, for example, a sodium salt of acrylic acid.

In certain aspects, the SAPH material of the invention further includes at least one of a (poly)vinyl or non-vinyl crosslinker. Many vinyl compounds having at least two polymerizable double bonds that can act as cross-linkers for the SAPH of the present invention are known, and include, for example, i) non-vinyl crosslinkers: agents having at least two functional groups capable of reacting with the carboxyl groups of the polymer, such as glycerin, polyglycols, ethylene glycol, diglycidyl ether, and aliamines. Additional, examples of these compounds are given in U.S. Pat. Nos. 4,666,983; 5,145,906; and 4,734,478; the disclosure of which are incorporated herein by reference in their entirety.

In an additional aspect, the invention encompasses methods of producing SAPH materials. In certain embodiments, the methods of invention include adding the non-vinyl cross-linkers homogeneously to the polymerization mixture at the start of the process prior to introduction of a fluid solvent. In any of the embodiments described herein, the non-vinyl crosslinker includes at least one of hexane diamine, glycerin, ethylene glycol diglycidyl ether, ethylene glycol diacetate, polyethylene glycol 400, polyethylene glycol 600, polyethylene glycol 1000 or combinations thereof. In another embodiment, the non-vinyl crosslinker comprises at least one of polyethylene glycol 400, polyethylene glycol 600 or other PEG material listed as generally recognized as safe or as may be otherwise approvable by the FDA or such similar regulatory authorities as acceptable for human ingestion applications.

The total amount of all crosslinkers present must be sufficient to provide a SAPH material with good absorptive capacity, good absorption under load, and high yields of the desired SAPH materials with extremely low concentrations of extractable materials from the final reaction product; including extremely low concentrations of residual monomers, low molecular weight oligomers, solvents and or other volatile organic material. As described herein, it is desirable that the monomers, comonomers, crosslinkers, etc., of the SAPH be preferentially soluble in the supercritical carbon dioxide phase of the preferred manufacturing method of the present invention, whereas the polymer and hydrogel will not be soluble. For lightly crosslinked applications, the crosslinkers may be present in an amount of at least about 500 parts per million; about 2500 parts per million; or about 5000 parts per million by weight based on the amount of the polymerizable monomer present. For more heavily cross-linked applications, the crosslinkers may be present in an amount of about 50,000 parts per million or less by weight; about 25,000 parts per million or less by weight; or about 10,000 parts per million or less by weight based upon the amount of the polymerizable monomer present.

In those embodiments of the present invention that utilize a blend of (poly)vinyl crosslinkers with non-vinyl and or dimodal crosslinkers, the solvation of all three types of crosslinkers is additive in nature. That is, if the amount of one crosslinker is increased the amount of another must be decreased to maintain the same overall solvation in the supercritical fluid phase. In addition, the proportion of the crosslinker components within the blend may be varied to achieve different SAPH properties and processing characteristics. This is especially important for an ingestible material that is to have its action occur within the gastric environment. If too little of the total crosslinker blend is composed of polyvinyl crosslinker the polymerized hydrogel may not have sufficient toughness to be easily ground, processed, and dried. For this reason the proportion of polyvinyl crosslinker in the total crosslinker blend is preferably at least sufficient to produce a hydrogel that has enough toughness to be readily ground, processed, and dried. This toughness is inversely proportional to the centrifuge capacity of the SAPH material after drying but before heat-treatment. The exact amount of crosslinker required in the blend to achieve this level of toughness will vary, depending on the preferred final intended use of the SAPH material.

Depending upon the swelling ratio of the SAPH used, practical volumes of ingested SAPH of the present invention in non-combination formats and some combination formats, would preferably be at least 250 milligrams per dose, more preferably be at least 500 milligrams per dose, and most preferably be at least 750 milligrams per dose, given with 6 to 12 oz water 30 to 60 minutes before meals.

An additional aspect the invention relates to methods for controlling appetite in an individual comprising administering or consuming an effective amount of a SAPH composition of the invention in a unitary dose, wherein the SAPH is effective for controlling appetite. In another embodiment the invention comprises a method for reducing weight in an individual comprising administering or ingesting an effective amount of the SAPH composition of the invention in a unitary dosage form as a temporary pre-meal gastric bulking agent to suppress appetite, and therefore, assist in weight loss and/or weight management and/or promote a feeling of early satiety in an individual. In still other aspects the invention relates to methods for reducing caloric intake in an individual comprising administering to or ingestion by an individual or consuming an effective amount of the polycarboxylate composition of the invention.

An "effective amount", "effective dose", "therapeutically effective amount", or "pharmaceutically effective amount" is that dose required to prevent, inhibit the occurrence, treat (alleviate a symptom to some extent, preferably all of the symptoms) or cause or promote the desired physiological change in an organism. The effective amount depends on the type of condition or disease, the composition used, the route of administration, the type of mammal being treated, the physical characteristics of the specific mammal under consideration, concurrent medication, and other factors which those skilled in the medical arts will recognize. Generally, an amount between 0.1 mg/kg and 1000 mg/kg body weight/day of claimed ingredients is administered/ingested depending upon the potency of the SAPH. In addition, effective amounts of the compositions of the invention encompass those amounts utilized in the examples to facilitate the intended or desired biological effect.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50.

In any of the aspects or embodiments described herein, an effective amount of the dietary supplement composition of the present invention may be administered or ingested at least once daily, and in any pharmaceutically acceptable dosage form known or which becomes known by those of skill in the art. In addition, the SAPH may be provided as a food additive or dietary supplement which can be administered by any pharmaceutically acceptable route recognized by those of skill in the art, for example, oral, enteral, parenteral, intravenous, transdermal, nasal, rectal, topical, vaginal or the like. In a preferred embodiment, the SAPH is provided as a food additive or dietary supplement of the invention and is a unitary dosage form suited for oral administration or consumption by an individual at least once per day, for example, in a capsule, tablet, caplet, soft gel capsule, controlled release tablet, powder, liquid, liquid or gel filled capsule, and the like.

In any embodiment described herein, the compositions of the invention can be administered together with any number of pharmaceutically acceptable excipients. In any of the SAPH or bulking composition embodiments described herein, the composition may contain from about 0.01% to about 80% by weight of an excipient. In certain embodiments, the SAPH or bulking agent compositions comprise from about 0.01% to about 5%, or 10%, or 15%, or 20%, or 25%, or 30%, or 40%, or 50%, or 60%, or 70% by weight of an excipient. The invention contemplates all amounts occurring between the identified ranges. One or more compositions of the invention can be present in association with one or more non-toxic pharmaceutically acceptable carriers and/or diluents and/or adjuvants, and if desired other active ingredients. The pharmaceutical compositions of the invention can be in a form suitable for oral use, for example, as tablets, troches, lozenges, aqueous or oily suspensions, dispersible powders or granules, emulsion, hard or soft capsules, or syrups or elixirs.

In any of the preferred embodiments the composition of the invention also comprises at least one of the following: a stabilizer or carrier, for example, cellulose, magnesium stearate, silica; a lipid; an oil; a salt; an acid; a base; an emulsifier; an excipient; a flavoring agent; or combinations thereof. The inert matrix of the present invention comprises at least one of the following: cellulose fiber (as BH 200), magnesium (as magnesium stearate), and silica. In certain embodiments, the composition of the invention comprises from about 0.01 mg to about 1000 mg of cellulose fiber. In other embodiments, the composition of the invention comprises from about 0.01 mg to about 1000 mg of L-Leucine.

Compositions intended for oral use can be prepared according to any method known to the art for the manufacture of pharmaceutical compositions and such compositions can contain one or more such sweetening agents, flavoring agents, coloring agents or preservative agents in order to provide pharmaceutically elegant and palatable preparations. Capsules, tablets or gel caps contain the active ingredient in admixture with non-toxic pharmaceutically acceptable excipients that are suitable for the manufacture of capsules, tablets or gel caps (i.e., soft gel capsules). These excipients can be for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example L-Leucine, magnesium stearate, stearic acid or talc.

In certain embodiments, the SAPH or bulking composition comprises from about 0.01% to about 20.00% by weight of stearic acid. In additional embodiments the SAPH or bulking composition comprises from about 0.01% to about 10.00% by weight of magnesium stearate. In still additional embodiments, the SAPH or bulking composition comprises from about 0.01% to about 20.00% by weight of magnesium silicate (i.e., talc).

Hydrophobic excipients, for example, surfactants, emulsifiers, lipids, detergents, lubricants, etc. . . . can, in some instances, delay the rate of SAPH or bulking composition swelling. Therefore, the invention also contemplates embodiments in which the excipients are hydrophilic. It is believed that hydrophilic excipients allow for the more rapid fluid absorption of the SAPH hydrogel (i.e., allows faster swelling) within the gastric environment. Accordingly, in certain additional embodiments, the SAPH or bulking composition comprises a hydrophilic excipients, for example, an amino acid excipient, such as for example, Leucine, or L-Leucine.

Leucine (abbreviated as Leu or L) is an α-amino acid with the chemical formula $HO_2CCH(NH_2)CH_2CH(CH_3)_2$. It is an essential amino acid, which means that humans cannot synthesize it. With a hydrocarbon side chain, leucine is classified as a hydrophobic amino acid. It has an isobutyl R group. Leucine is a major component of the sub units in ferritin, astacin and other 'buffer' proteins. As an essential amino acid, leucine is not synthesized in animals, hence it must be ingested, usually as a component of proteins. It is synthesized in plants and microorganisms via several steps starting from pyruvic acid. Leucine has been found to slow the degradation of muscle tissue by increasing the synthesis of muscle proteins. Leucine is utilized in the liver, adipose tissue, and muscle tissue. In adipose and muscle tissue, leucine is used in the formation of sterols, and the combined usage of leucine in these two tissues is seven times greater than its use in the liver. As a food additive L-Leucine has E number E641 and is classified as a flavor enhancer. In studies in which Leucine was injected directly into the brains of rats, the appetite of the rats was reduced. Evidences from several studies, on rats, suggest that leucine is involved in protein synthesis in the skeletal muscle, and slows muscle degradation. In addition, Leucine is rapidly soluble in aqueous environments such as those that exist in the stomach. In particular, micronized Leucine is a known dietary supplement taken by body builders to improve muscle development, and is almost instantly soluble in water. Micronized Leucine is a powder that demonstrates a smooth or "slick" feel to the touch, and can behave similarly to a lubricant in the formulation of the composition of the invention.

The addition of Leucine in the SAPH or bulking compositions of the invention results in surprising and unexpected synergism when formulated and administered with the compositions of the present invention because it allows for faster swelling of the polymer hydrogel, and further enhances appetite modulation and muscle mass. Additional advantages of using Leucine include its low cost, availability, safety and GRAS status as a food additive, and purity. In particular, the use of micronized L-Leucine is readily available and is amenable for use in the formulations of the present invention. In any of the embodiments described herein, the SAPH or bulking compositions of the invention comprises from about 0.5% to about 50% of at least one of Leucine, or L-leucine, or micronized L-leucine, or a combination thereof. In certain additional embodiments, the SAPH or bulking composition of the invention comprises from about 1% to about 15% of at least one of Leucine, or L-leucine, or micronized L-leucine, or a combination thereof. In an additional embodiment, the SAPH or bulking composition of the invention comprises about 5% of at least one of Leucine, or L-leucine, or micronized L-leucine, or a combination thereof.

The capsules, tablets or gel caps can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monosterate or glyceryl disterate can be employed.

Formulations for oral use can also be presented as hard gelatin capsules wherein the effective ingredient is mixed with an excipient or inert solid diluent, for example, calcium carbonate, calcium phosphate or kaolin, or as soft gelatin capsules wherein the active ingredient is mixed with water or an oil medium, for example peanut oil, liquid paraffin or olive oil. In addition, in any of the embodiments the composition of the invention may further comprise a diluent, or other additive, such as binders, fillers, supports, thickening agents, flavoring agents, gums, coloring agents, preservatives, stabilizers, regulators, emulsifiers, flow agents, lubricants, absorbents, and the like or combinations thereof. In still another embodiment, the composition of the invention may comprise a dietary fiber supplement, for example cellulose, glucomannan, oat bran or other natural fiber source. The present invention includes compositions prepared for storage or administration which include a pharmaceutically effective amount of the desired compounds in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985) hereby incorporated by reference herein. For example, preservatives, stabilizers, dyes and flavoring agents can be provided. These include sodium benzoate, sorbic acid and esters of p-hydroxybenzoic acid. In addition, antioxidants and suspending agents can be used.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin or other natural sweeteners like Stevia®.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavoring agents can be added to provide palatable oral preparations. These compositions can be preserved by the addition of an anti-oxidant such as ascorbic acid or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present. Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example glycerol, propylene glycol, sorbitol, glucose or sucrose. Such formulations can also contain a demulcent, as well as preservative and flavoring and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables.

Beginning with U.S. Pat. No. 2,649,439 issued to Brown in August 1953, numerous examples in the prior art, as extensively disclosed by the applicant above, have described the manufacture of SAPH polymeric materials. Brandt in U.S. Pat. No. 4,654,039 and Re. 32,649, discloses a process for the preparation of SAPH resins and the use of known crosslinking agents for such materials. A variation of the basic process is taught in GB Patent 2,119,384, which discloses a post-polymerization surface crosslinking process in which the previously polymerized absorbent resin powder is mixed with crosslinkers, preferably polyalcohols, a solvent and water, to coat the resin surface, and heated to temperatures in the range of 90 to 300° C. to crosslink the surface. U.S. Pat. No. 5,506,324 discloses polymeric resin particles comprising polymers containing carboxyl moieties which are crosslinked using C2-10 polyhydric hydrocarbons which are ethoxylated with from 2 to 8 ethylene oxide units per hydroxyl moiety of the ethylene oxide chain wherein the hydroxyl moiety at the end of each chain is esterified with a C2-10 unsaturated carboxylic acid or ester thereof. In a preferred embodiment, the SAPH resin particles are subjected to heat-treatment after drying and sizing.

Numerous other examples of similar approaches to the manufacture of SAPH materials are cited in the prior art. However, each is plagued with the problem of having the presence of excessive amounts of impurities in the form of residual heavy metals, and or residual monomers, and or residual low molecular weight oligomers, and or residual solvents; which render the final material too toxic, too carcinogenic or otherwise unacceptable by regulators for human ingestion and consumption in the anticipated amounts necessary to construct a suitable SAPH as required by the present invention.

Accordingly, it is desirable to have a process for preparing a SAPH material with reduced residual monomer and low molecular weight oligomers concentrations; reduced residual solvent concentrations; and reduced heavy metal concentrations which would not be toxic or carcinogenic and would be scientifically and medically acceptable for human ingestion and consumption within the recommended dosage range for a SAPH material sued for the purposes of providing temporary, pre-meal gastric bulking to assist in appetite suppression and weight management.

Therefore, in another aspect, the present invention relates to a process by which a SAPH material can be manufactured such that it has: a) low residual monomer and low molecular weight oligomer concentrations; and b) low residual solvent concentrations, including low residual organic volatiles concentrations, and c) low heavy metal concentrations whereby the final material is non-toxic, non-carcinogenic and acceptable by regulators for human ingestion and consumption for the purposes of providing temporary, pre-meal gastric bulking to assist in appetite suppression and weight management.

In an embodiment of this aspect of the invention, the process comprises (i) polymerizing a monomer or a monomer mixture in a polymerization mixture comprising: (a) one or more ethylenically unsaturated carboxyl-containing monomers, (b) one or more crosslinking agents, and (c) a polymerization medium consisting of a supercritical fluid solvent, to form a crosslinked hydrogel, (ii) venting the supercritical fluid solvent which contains undesirable or excessive concentrations of reaction products, (iii) comminuting the hydrogel to resinous particles (iv) drying the hydrogel to form resinous crystals, (v) mesh sorting the resinous crystals to a preferred particle size; and (vi) heat treating the resinous crystals.

In certain embodiments, the SAPH material produced according to the methods of the invention comprises a cumulative residual monomer and low molecular weight oligomer content of less than about 50 ppm; less than about 10 ppm; and/or less than about 2 ppm, based on the weight of the solid polymer. The residual amounts are significantly less than the regulatory standards imposed for maximum concentrations of any such particular monomers as are regulated for daily expose limits as used in the embodiments of the present invention.

In certain embodiments, the SAPH material produced according to the methods of the invention comprises a residual organic volatiles and or solvents content less than about 50 ppm; less than about 10 ppm; and/or less than about 1 ppm, based on the weight of the solid polymer. The residual amounts will be significantly less than the regulatory standards imposed for maximum concentrations of any such particular solvents or organic volatiles as are regulated for daily expose limits as used in the preferred embodiments of the present invention.

In certain embodiments, the SAPH material produced according to the methods of the invention comprises a residual heavy metals content less than about 10 ppm; less than about 5 ppm; and/or less than about 1 ppm, based on the weight of the solid polymer. The residual amounts will be significantly less than the regulatory standards imposed for maximum concentrations of any such particular metals as are regulated for daily expose limits as used in the preferred embodiments of the present invention.

Various processes have been used to attempt removal of unwanted manufacturing by-products and toxic contaminants from SAP materials. For example, in the past fluid bed dryers have been used to reduce residual solvent. Unfortunately, these methods are unable to reduce residual solvents to below about 10 ppm and such drying methods can take several days to eliminate enough residual solvent to meet current regulatory mandates. In addition, drying methods are both expensive and time-consuming. Furthermore, drying methods are only useful for volatile materials and are not capable of eliminating non-volatile materials in the form of either residual monomers, low molecular weight oligomers or toxic heavy metals; and thus the exclusive use of drying methods would be precluded as an appropriate choice for manufacturing a SAPH into an acceptable ingestible form.

Second, azeotropic distillation (AD) techniques have been variously described and are well known to those skilled in the art. AD is used to remove organic solvents from aqueous suspensions of polymers. However, the AD process functions only if the organic solvent has a certain degree of water-solubility, which is frequently not the case when purifying SAPH materials where the solvents are trapped within the porous domains of the cross-linked hydrogel matrix material. Of significance, AD techniques are also not useful in removing unwanted residual monomers, low molecular weight oligomers or heavy metals. Therefore, AD methods would not be suitable for removing the unwanted contaminants found in commercially available SAP materials as is required for the preferred use of this invention.

Third, organic solvents can be extracted by other organic solvents. If the extractant is not water-soluble, it in turn has to be removed in an additional step. If it is water-soluble, it can be removed by washing the material with water. However, the by-product is large amounts of contaminated wastewater that has to be removed, which increases process costs significantly. Furthermore, AD does nothing to remove unwanted residual monomers low molecular weight oligomers, or heavy metals.

Fourth, organic solvents can also be removed via steam-treatment. However, the use of steam poses technical problems because the intensive thermal stress of the steam can collapse the pore structure of the SAPH material if the softening point of the polymer network is exceeded.

Fifth, supercritical fluid extraction (SFE) methods and its variants have been applied as a separate step in polymer purification and such methods are disclosed in the prior art. However, of importance to this invention, no prior art disclosure provides for the use of a supercritical fluid medium being incorporated as the organic phase solvation step in the manufacture of SAPH materials, especially as such pertains to the intended use herein. The cost-savings advantages, product yield, and simplicity of the method disclosed in this present invention provide compelling improvements and inventive advancements in the art of manufacturing ultra-pure SAPH materials.

Sixth, European Patent Publication 505 163 relates to a method of reducing residual (meth)acrylic acid present in polyacrylic acid SAPH gel polymers that comprises treating the polymers with a combination of a surfactant having a certain HLB and a vinyl addition compound that can react with a vinylic double bond. Examples of the vinyl addition compound include sulfites and bisulfites. However, this method does not remove excess solvents or heavy metals.

U.S. Pat. No. 5,629,377 discloses SAPH materials with high absorption values and low residual monomer levels. The material is prepared by polymerizing unsaturated carboxyl containing monomers in the presence of a chlorine or bromine-containing oxidizing agent to form a hydrogel that is then heated to a temperature preferably from 210° C. to 235° C. Although the method is effective for improving absorbency, the high heat treat temperature needed to activate the chlorine or bromine-containing oxidizing agent is detrimental for various reasons, including energy cost and loss of moisture. Neither does the process reduce residual solvent or other volatile concentrations to acceptable levels.

U.S. Pat. No. 6,914,099 discloses SAPH polymers having reduced levels of residual monomer produced using a peroxodisulfate salt additive in the manufacturing process. Such additive is toxic, expensive and does not remove low molecular weight oligomers, residual solvents or heavy metals. Rebre, et. al. in U.S. Pat. Nos. 5,373,066, 5,408,006, 5,442,014, and 5,563,218 discloses water absorbent polymers having reduced levels of residual monomer produced using hydrogen peroxide as an additive in the manufacturing process. Similarly, such disclosures fail to describe a reduction of solvents and other volatiles, and heavy metals to acceptable levels for the purposes described herein.

Additional aspects and embodiments will be evident to the skilled artisans from a review of the appended non-limiting examples. The accompanying examples, which are incorporated into and form a part of the specification, illustrate several embodiments of the present invention and, together with the description, serve to explain the principles of the invention. The examples are only for the purpose of illustrating an embodiment of the invention and are not to be construed as limiting the invention.

Exemplary Polymerization Method of SAPH Materials:

The present invention discloses the use of a supercritical fluid environment in order to form the solvent of choice for the polymerization medium. The choice of the polymerization medium and the selection of a supercritcial solvent would be beneficial where the monomers and other starting raw materials and manufacturing materials are soluble in said solvent and the desired final polymers are insoluble. In addition, the supercritical solvent must be inert to the monomers and the polymers, and will preferably have the same solvation characteristics as an aromatic or aliphatic hydrocarbon or a halohydrocarbon as are typically used in the organic phase of such polymerization reactions well known in the prior art.

Although those skilled in the art will recognize that other supercritical fluids would be effective for the uses described herein, the most preferable supercritical fluid polymerization medium of the present invention will be comprised of carbon dioxide ($CO_2$). $CO_2$ is characterized as a non-polar solvent with solubility parameters similar to hexane. It does, however, have some affinity with slightly polar molecules because of its molecular quadrupole. Carbon dioxide is also selected as the most preferred solvent in the supercritical fluid method disclosed herein due to its convenient critical temperature (31.3° C.) and pressure (7.4 MPa), low cost, low toxicity, ease of distillation and recycling, and non-explosive character.

Those skilled in the art will recognize that the use of a supercritical fluid as the solvent in the polymerization medium may be further enhanced by the addition of other liquid or liquefiable solvents to the reaction chamber. These solvents called, modifiers, can be added to the supercritical carbon dioxide medium as well in order to increase solubility or enhance displacement of the desired extractants from the SAPH matrix while still confined in the pressurized reaction container. Common modifiers useful in the methods of the invention include methanol, benzene, hexane, chloroform and others. It is desirable that the selected modifier act by swelling the polymer to increase diffusion and extraction rates as well as having appropriate levels of acceptability as an ingestible material at the reduced residual levels made available by the present invention. Modifiers useful in the methods of the invention include non-polar or aromatic as well as polar. Therefore, it is desirable that the modifier selected will enhance extraction even when solubility is not a limiting factor. It is also desirable that the selected modifiers be ingestible and non-toxic, and otherwise acceptable by regulatory authorities for the disclosed intended use of this present invention. In certain embodiments of the method of the invention, the modifier comprises at least one of cyclohexane, hexane, methanol, or a combination thereof. Methanol is useful because of its low toxicity and ability to cause significant swelling in the SAPH materials of the present invention in the supercritical phase, its volatility upon distillation, and easy recycling in the manufacturing process.

In addition to the incorporation of modifiers, those skilled in the art will recognize that the concomitant use of ultrasound or microwave heating methods as are disclosed in the prior art may further improve the efficiency of the purification of the SAPH matrix.

Typically the polymerization phase of the manufacturing process for SAPH materials involves the introduction of a free radical or oxidation reduction (redox) catalyst system usually a chlorine- or bromine-containing oxidizing agent under conditions such that a crosslinked hydrophilic material is prepared. The free radical initiator may be any conventional water soluble free radical polymerization initiator including, for example, peroxygen compounds such as sodium, potassium and ammonium persulfates, caprylyl peroxide, benzoyl peroxide, hydrogen peroxide, cumene hydroperoxide, tertiary butyl diperphthalate, tertiary butyl perbenzoate, sodium peracetate and sodium percarbonate. In certain embodiments of the method of the invention, the redox catalyst is hydrogen peroxide, which has low ingestible toxicity.

Conventional redox initiator systems can also be utilized. These systems can be formed by combining the foregoing peroxygen compounds with reducing agents, such as, for example, sodium bisulfite, sodium thiosulphate, L- or iso-ascorbic acid or a salt thereof, or ferrous salts. In certain embodiments, about 5 mole percent or less of the initiator can be employed, based on the total moles of polymerizable monomer present. In other embodiments, from about 0.001 to about 0.25 mole percent; or from about 0.25 to about 1.0 mole percent of initiator is employed, based on the total moles of polymerizable monomer to be polymerized in the supercritical fluid medium. In certain embodiments of the invention, the reducing agent is sodium bisulfate, which has low ingestible toxicity.

In one embodiment wherein the dried hydrogel is subjected to heat-treatment, the process may be conducted in the presence of a chlorine- or bromine-containing oxidizing agent. The selection of the chlorine- or bromine-containing oxidizing agent if used will need to be compatible with the acceptable ingestion criteria as stated herein. The chlorine- or bromine-containing oxidizing agent is present in an amount such that after heat-treatment the desired balance of resin properties is achieved. In certain embodiments, the method comprises including at least about 10 ppm by weight of a chlorine- or bromine-containing oxidizing agent, based on the total weight of monomers; at least about 50 ppm; at least about 100 ppm; or at least about 200 ppm. It is desirable that the amount of a chlorine- or bromine-containing oxidizing agent employed is about 2000 ppm or less by weight based on the total weight of monomers present; is about 1000 ppm or less; is about 800 ppm or less; or is about 500 ppm or less. The chlorine- or bromine-containing oxidizing agent is preferably dissolved or dispersed in the polymerization mixture prior to initiation of the polymerization. However, it may also be applied as an aqueous solution to the hydrogel.

Modified Method of Inverse Suspension Polymerization

The SAPH materials of the present invention such as crosslinked poly(acrylic acid) can be synthesized by inverse suspension polymerization techniques modified to accept a supercritical fluid substituted for the organic phase solvent. In one embodiment of this method of the invention an aqueous phase containing a preferred partially neutralized acrylic acid, a crosslinking agent, and an initiator agent are dispersed in the supercritical fluid phase and stabilized by a surfactant. The inverse suspension can be carried out using supercritical $CO_2$ as the organic phase solvent. In an embodiment, the polymerization can be initiated by sodium or potassium persulfate with PEG 400 or PEG 600 as the preferred crosslinkers, using methanol as the modifier, and using sorbitan monooleate as the surfactant. In certain embodiments, the degree of neutralization of the monomer is from about 25% to about 50%; or about 75%.

In an embodiment of this method of the invention, the process is performed in a batch manner wherein all of the reaction materials are contacted and the reaction proceeds with the intermittent or continuous addition of one or more of the components, including the supercritical $CO_2$ fluid acting as the solvent is either pulsed intermittently or continuously cycled through the polymerization medium for the synchronous and or simultaneous removal of solublized and or suspended by-products, contaminants and other unwanted residuals targeted for removal. During the reaction period the polymerization mixture is continuously subjected to polymerization conditions that are sufficient to produce the SAPH's resinous particles in ultra-pure form by the venting, distilling and recycling the $CO_2$ in order to continuously remove any of the undesirable contaminants and excessive concentrations of unused raw materials and undesirable reaction by-products.

Traditional inverse suspension polymerization procedures as described in greater detail in Obayashi et al., U.S. Pat. No. 4,340,706, and in Flesher et al., U.S. Pat. No. 4,506,052, allow for the addition of other ingredients such as surfactants, emulsifiers and polymerization stabilizers, however, when employing organic solvents, as is necessary to form the SAPH materials of this invention, these traditional methods require that the hydrogel-forming polymer material is recovered from such processes and is separately treated to remove substantially all of the excess organic solvent, heavy metals and residual monomer and low molecular weight oligomers. Furthermore, such materials generally absorb the entire aqueous reaction medium during the process requiring: 1) shaping by an agitator; 2) recovery from the reaction medium by azeotropic distillation and/or filtration followed by drying. If recovered by filtration, then some means of removing the solvent present in the hydrogel must be used.

Such means are commonly known in the art. These additional steps are obviated by the present invention's use of supercritical fluid reactions most preferably using $CO_2$ or other suitable material.

Reaction Temperature—Cycling Method:

Poly(acrylic acid), as a SAPH material encompassed by the present invention has a relatively high glass transition temperature of approximately 102° C. Its manufacture may be performed at any temperature at which polymerization occurs recognizing that under supercritical fluid conditions, the glass transition temperature may be depressed. The supercritical phase requires an environment of increased pressures sufficient for maintenance of the supercritical phase. The temperatures must be elevated as well; preferably to at least about 25° C.; at least about 50° C.; or at least about 75° C. However, under the method of the present invention, the polymerization medium is intermittently spiked to a temperature that is simultaneously: a) below the apparent glass transition temperature of the SAPH material being produced under supercritical conditions, and b) above the boiling points of the preferred solvents, surfactants and modifiers added, and c) above the solvation temperature and melting point of the monomer(s) targeted for reaction and subsequent removal.

An additional benefit of the use of supercritical environment of the present invention allows for a reduction of the optimum operating temperature of the polymerization reaction. The supercritical environment not only improves polymerization efficiency, and reaction yields; the temperature lowering substantially lowers manufacturing costs and saves energy.

Reaction Pressure—Cycling Method:

The reaction may be performed at any pressure above carbon dioxide's supercritical fluid pressure (7.4 MPa) and at which polymerization occurs. In certain embodiments of the method of the invention the reaction is performed at a pressure of at least about 10 MPa; at least about 15 MPa; or at least about 25 MPa. However, in no case will the reaction pressure be of sufficient magnitude to reduce reaction yields, as for example by lowering the reaction temperature to a sub-threshold glass transition point that would effect efficient polymerization. In another embodiment, the process utilizes pressure cycling to reduce and increase temperatures within the reaction container. Adding a recycled purified distillate charge of $CO_2$ under pressure controllably increases the reaction temperature and provides a solvent medium free of targeted residuals, thus driving the equilibrium toward a maximally rapid uptake of newly formed solvate from the polymerization medium. Venting the supercritical $CO_2$ controllably promotes a temperature decline within the reaction container. Thus the synchronous cycling of pressures, temperatures, newly introduced charges of $CO_2$ and reaction materials allows for a maximally efficient polymerization/solvation environment while simultaneously maximally removing unwanted impurities and targeted contaminants resulting in ultra-pure SAPH materials of the present invention.

Reaction Time:

The reaction is conducted for a time sufficient to result in the desired conversion of monomer to crosslinked hydrophilic resin. Preferably, the conversion is at least about 95 percent; at least about 98 percent; or at least 99.99 percent. A diminishing returns cost analysis is essential to determine the overall time requirements based upon the desired purity and throughput for the commercial manufacturing of the SAPH material. In certain embodiments the maximum reaction time is not more than about 6 hours; not more than about 3 hours; or not more than about 1 hour.

Neutralization:

In any of the embodiments of the process described herein, at least about 25 mole percent; at least about 50 mole percent; or at least about 65 mole percent of the carboxylic acid units of the SAPH material are neutralized with base. This neutralization may be performed before or after completion of the polymerization. In an embodiment the starting monomer mix has carboxylic acid moieties which are neutralized to the desired level prior to polymerization. The final polymer or the starting monomers may be neutralized by contacting them with a salt-forming cation. In any of the embodiments described herein, the salt-forming cations include: an alkaline metal; ammonium, substituted ammonium, or amine based cations; an alkali metal hydroxide such as, for example, sodium hydroxide or potassium hydroxide, or an alkali metal carbonate such as, for example, sodium carbonate or potassium carbonate. In still another embodiment, the starting monomers are neutralized with sodium hydroxide to 75 mole percent.

Fine Spiking Method:

It is also possible to prepare the SAPH of the present invention by adding recycled "fines" to the polymerization mixture. "Fines" are generally considered to include, but are not limited to, the fraction of SAPH resin particle that passes through a 140 mesh screen when the dried and ground product is screened prior to heat-treatment. The amount of fines added to the polymerization mixture is, on a total solids basis, preferably less than about 12 weight percent; less than about 10 weight percent; or less than about 8 weight percent. This method improves the reaction yields and reduces manufacturing losses of the resins made and concomitantly reduces the costs of manufacture of the final SAPH material.

Method of Comminution:

After removal from the reactor, the SAPH material is subjected to comminution by a convenient mechanical means of particle size reduction, such as grinding, chopping, cutting or extrusion as are commonly employed by those skilled in the art. The size of the final particles after particle size reduction should be such that homogeneous drying of the particles can occur. Depending upon the intended use of the SAPH of the present invention, desired particle sizes will range from a smallest convenient size of approximately 100 to 250 microns for the finest powders, used for example as in some mixes and nutrition bars; up to a largest convenient size of approximately 750 to 1,000 microns for use in certain puddings. Therefore, the preferred particle sizes of the undried material range from 0.05 to 0.5 mm, or other such size as will provide fine resinous crystals or powders of a desired particle size upon drying. This particle size reduction can be performed by any means known in the art that gives the desired result. Preferably, the particle size reduction is accomplished by chopping. Most preferably, the particle size reduction is accomplished by grinding. Final size selection is accomplished by serial mesh screening techniques as are well known in the art, with "fines" collected for reuse as described above. It is desirable to reduce the amount of fine powder form in the final SAPH mix to reduce the inhalable dust used in further processing into capsules or other products as an occupational safety and environmental safety factor for the workers who would potentially be exposed to such dusts.

Exemplary Heat Treatment Method:

In order to improve the swelling efficiency of high molecular weight crosslinked polycarboxylic acids, crosslinked SAPH materials are traditionally subjected to heat treatment. These SAPH materials, in the form of the suspension obtained in the polymerization, can be treated at from 80 to 130° C. Traditionally, if the polymerization has been carried out using a suspending agent whose boiling point is above 80° C., the polymer suspension is heated in an autoclave under superatmospheric pressure. However, this separate step is obviated by the present invention where the polymerization is conducted under supercritical conditions and is a benefit thereof. During the heating of the SAPH of the present invention, the SAPH is slowly isolated as a solid during this heating step as the supercritical fluid is vented off, and with the reactor's temperature and pressure being slowly reduced to over the course of the heating to become ambient temperature and atmospheric pressure during the steady drying. As the supercritical $CO_2$ is vented off it is replaced with a nitrogen atmosphere in order to avoid damaging the SAPH by oxidation. Traditional heat treatments typically require the introduction of another solvent to aid in the extraction of benzene or other unwanted polymerization solvents. This step is unnecessary due to the practice of the present invention and is yet another benefit thereof. In certain embodiments, the crosslinked SAPH of the present invention is exposed to heat in the reaction chamber at from about 80° C. to about 130° C.; or from about 90° C. to about 120° C. It is desirable that the treatment temperatures be maintained below the glass transition temperature of the SAPH, so that the SAPH does not agglomerate during heating, which in the case of the most preferred embodiment of the present invention would be a temperature not to exceed 102° C. The duration of the heat treatment of the SAPH of the present invention is from 2 minutes to 5 hours, relatively long treatment times being suitable at 80° C. and very short ones at no more than 102° C. If the crosslinked SAPH is heated for too long a time, its swelling ratio in aqueous systems is reduced, and can fall to virtually 0, because the polymer is then no longer swellable.

Exemplary Drying Method:

After heat treatment the hydrogel particles are subjected to drying conditions to remove any remaining polymerization medium, carbon dioxide, volatile monomers and low molecular weight oligomers, dispersing liquid, surfactants, residual solvent and substantially all of the unconsumed water. Preferred dryers are fluidized beds or belt dryers. Alternatively, a drum dryer may be used. Such techniques especially those assisted by vacuum systems are well known in the art. The optimal temperature at which the drying takes place is a temperature high enough such that any remaining: polymerization medium and liquid, including water; modifiers, surfactants and any optional solvents, are removed in a reasonable time period. The drying temperature should be high enough to remove any and all anticipated volatiles, but not so high as to cause degradation of the SAPH material; i.e., ideally not to exceed the SAPH material's glass transition temperature. Desirably, the ambient temperature of the SAPH particles of the present invention during drying is always maintained at about 50° C. or greater; at about 75° C. or greater; at about 90° C. or greater; or at about 100° C. However, the drying temperature for the SAPH of the most preferred embodiment of this invention shall always remain just below its glass transition temperature being less than 102° C. The drying time should be sufficient to remove substantially all of the remaining unwanted reaction components, water and any undesirable volatile impurities. Preferably, a minimum time for drying is at least 10 minutes, with at least 15 minutes being preferred. Preferably, the drying time is 60 min or less, with 25 min or less being more preferred. In certain embodiments, drying is performed under conditions such that water, and optional solvent, volatilizing away from the absorbent resin particles is maximally removed. Such removal can be maximally achieved by vacuum techniques or by passing inert gases such as nitrogen or dehumidified heated air over or through the layers of resin particles. In certain embodiments, drying occurs in dryers where air heated at from about 70 to 90° C. is blown through or over layers of the resin particles under vacuum. Exemplary dryers useful in methods of the invention include, for example, fluidized beds, belt dryers, or drum dryers. In any event, the drying time should be sufficient to remove any remaining volatiles to levels below the acceptable exposure limits as an ingestible material as such are established by jurisdictional regulatory authorities.

Moisture Content:

After drying, in certain embodiments of the invention the moisture content of the SAPH material between zero and about 20 weight percent; less than about 20 weight percent; less than about 10 weight percent; or less than about 5 weight percent. Therefore, immediately upon drying and cooling to room temperature, a quality assurance sample is removed from the batch based on SQL protocols, then the SAPH material of the present invention is wrapped in moisture barrier method, preferably a double-lined container and sealed along with an anhydrous moisture barrier pack (as are commonly used by those in the art) to protect against moisture accretion. The containers should not be reopened until ready for further manufacturing processing uses.

Exemplary SAPH Compositions:

SAPH particles produced according to the described modified inverse polymerization method using supercritical conditions in the polymerization medium of the present invention have exceptionally low levels of: a) residual monomers, residual low molecular weight oligomers; (see Table 3 Residual Monomer), b) residual solvent, (see Table 4 Residual Solvent and Volatiles), and c) heavy metals—especially the four toxic heavy metals most closely regulated; being arsenic, cadmium, lead and mercury (see Table 5 Residual Metals). A considerable advantage of the present manufacturing process is that the solvation and purification are conducted simultaneously as the excess monomers, volatiles and heavy metals are preferentially and selectively suspended in the supercritical carbon dioxide phase; and are subsequently taken up and removed upon venting of the carbon dioxide. Additionally, this process allows for easy distillation and recycling of the solvent material which reduces costs and minimizes hazardous environmental wastes. The final drying step completes the removal of any and all remaining volatiles; usually to levels below the detection limits of the most sensitive analytical equipment available.

Method of Purity Analysis:

The purity of the SAPH of the present invention was analyzed by state of the art methods and protocols conducted by Bodycote Testing Group located at their Health Science and Analytical Division, 9240 Santa Fe Springs Road, Santa Fe Springs, Calif., 90670. The testing for each of the three classes of by-products was performed as follows (the results of these tests are found in tables 3, 4, and 5):

TABLE 2

Testing Summary.

| Material Class | Analytical Method |
|---|---|
| Monomers and Oligomers | Gas Chromatography/Flame Ionization |
| Solvents and Organic Volatiles | Gas Chromatography/Mass Spectrometry SOP 5030 Rev 5 |
| Metals | Inductively Coupled Plasma - Mass Spectrometry SOP 7040 Rev 9 |

TABLE 3

Residual Monomer Analysis
Gas Chromotography/Flame Ionization

Free Acrylic Acid

| Results | 33.2 ppm |
|---|---|

Acrylamide

| Results | 0.3 ppm |
|---|---|

Sample ID: Lot # PS 100-07-12-01-1

TABLE 3

Residual Solvent and Volatiles Analysis
Volatiles Analysis
Residual Solvents by SOP 5030, Rev 5
Gas Chromatography/Mass Spectrometry
Parts per Million (μg/g)
Lot # PS100-07-12-01-1

| Analyte | Detection Limit (ppm) | Result |
|---|---|---|
| 1,4-Dioxane | 0.2 | ND |
| Acetone | 0.2 | ND |
| Acetonitrile | 0.2 | ND |
| Benzene | 0.2 | ND |
| Chloroform | 0.2 | ND |
| Ethanol | 0.2 | ND |
| Ethyl acetate | 0.2 | ND |
| Ethyl ether | 0.2 | ND |
| Freon-113 | 0.2 | ND |
| Heptane | 0.2 | ND |
| Hexane | 0.2 | ND |
| Isopropanol | 0.2 | ND |
| Isopropyl acetate | 0.2 | ND |
| Methanol | 0.2 | ND |
| Methyl ethyl ketone | 0.2 | ND |
| Methyl isobutyl ketone | 0.2 | ND |
| Methyl tert-butyl ether | 0.2 | ND |
| Methylene chloride | 0.2 | ND |
| Pyridine | 0.2 | ND |
| Tetrahydrofuran | 0.2 | ND |
| Toluene | 0.2 | ND |
| Trichloroethylene | 0.2 | ND |

TABLE 4

Residual Heavy Metals Analysis.
Metals Screen by SOP 7040, Rev 9
Inductively Coupled Plasma - Mass Spectrometry
Sample ID: SWELL PS-100, Lot# PS100-07-12-01-1
Metals of Greatest Regulatory Concern
Arsenic, Cadmium, Lead, and Mercury

| | Detection | Exposure Limit | | Max Daily Exposure Limit (70 kg Person) | | |
|---|---|---|---|---|---|---|
| | ppm (ug/g) | Limit (ppm) | (ug/kg bw/d) | Limit (ug) | Max Dose (ug) | % of Limit |
| Arsenic | ND | 0.01 | 0.050 | N/A | | |
| Cadmium | ND | 0.01 | 0.200 | | | |
| Lead | ND | 0.01 | 0.150 | | | |
| Mercury | 0.049 | 0.01 | 0.100 | 7.000 | 0.22 | 3.1% |

Other Metals

| List of Metals | ppm (μg/g) | Detection Limit |
|---|---|---|
| Aluminum | 7.3 | 0.50 |
| Antimony | ND | 0.01 |
| Barium | 0.12 | 0.08 |
| Beryllium | ND | 0.01 |
| Bismuth | ND | 0.01 |
| Boron | ND | 0.10 |
| Bromine | ND | 0.70 |
| Calcium | 19.00 | 10.00 |
| Cerium | ND | 0.01 |
| Cesium | ND | 0.01 |
| Chromium | 0.076 | 0.01 |
| Cobalt | ND | 0.01 |
| Copper | ND | 0.04 |
| Dysprosium | ND | 0.01 |
| Erbium | ND | 0.01 |
| Europium | ND | 0.01 |
| Gadolinium | 0.072 | 0.01 |
| Gallium | ND | 0.01 |
| Germanium | ND | 0.01 |
| Gold | ND | 0.01 |
| Hafnium | ND | 0.01 |
| Holmium | ND | 0.01 |
| Iodine | 1.70 | 0.01 |
| Iridium | ND | 0.01 |
| Iron | 1.00 | 0.50 |
| Lanthanum | 0.052 | 0.03 |
| Lithium | 0.034 | 0.01 |
| Lutetium | ND | 0.02 |
| Magnesium | ND | 8.00 |
| Manganese | 0.019 | 0.01 |
| Neodymium | ND | 0.01 |
| Nickel | 0.054 | 0.01 |
| Niobium | ND | 0.01 |
| Osmium | ND | 0.01 |
| Palladium | ND | 0.01 |
| Phosphorus | ND | 3.00 |
| Platinum | ND | 0.01 |
| Potassium | 230 | 2.00 |
| Praseodymium | ND | 0.01 |
| Rhenium | ND | 0.01 |
| Rhodium | ND | 0.01 |
| Rubidium | 0.029 | 0.01 |
| Ruthenium | ND | 0.01 |
| Samarium | ND | 0.01 |
| Selenium | ND | 1.00 |
| Silver | ND | 0.01 |
| Sodium | MATRIX | |
| Strontium | ND | 0.40 |
| Tantalum | ND | 0.01 |
| Tellurium | ND | 0.01 |
| Thallium | ND | 0.02 |
| Thorium | ND | 0.01 |
| Thulium | ND | 0.01 |
| Tin | ND | 0.01 |
| Titanium | 0.21 | 0.02 |
| Tungsten | ND | 0.01 |

TABLE 4-continued

Residual Heavy Metals Analysis.

| | | |
|---|---|---|
| Uranium | ND | 0.01 |
| Vanadium | ND | 0.02 |
| Ytterbium | ND | 0.01 |
| Yttrium | ND | 0.01 |
| Zinc | ND | 0.20 |
| Zirconium | 0.069 | 0.01 |

In one embodiment, the SAPH of the invention comprises an ultrapure SAPH material in the form of a polyacrylic acid hydrogel lightly cross-linked with polyethylene glycol 400 as a pre-meal temporary ingestible gastric bulking agent used to mitigate hunger. Particularly the SAPH of the present invention is useful as an ingestible weight-loss and weight management means to aid in suppressing appetite and/or promoting a feeling of early satiety in persons seeking to reduce their caloric intake, i.e., meal portion sizes, without a experiencing a residual feeling of hunger. The further objects of the present invention include the moderation of the gastric signaling mechanisms that acutely control appetite and the sensation of fullness, and additionally for use as a long term means of modifying eating behavior useful as a weight management tool, thus providing an adjunct to assist persons seeking to lose and or manage their weight. Furthermore, the present invention is not intended to be limited to human use, whereby veterinary uses are also considered.

Exemplary Dosage and Administration:

As recognized by those skilled in the art, since pure SAPH materials of the present invention are bio-inert, non-toxic, and meet all of the generally recognized as safe criteria; the practical and commercial limitations for the intended use of this disclosure relate most specifically to the presence of unacceptable levels of post-manufacture concentrations of impurities and contaminants commonly identified within the commercially available SAPH materials disclosed in the prior art. Governed by the specific limitations imposed by the prevailing jurisdictional regulatory bodies that monitor ingestion uses among each of the three classes of common SAPH contaminants (residual monomers and residual low molecular weight oligomers, residual solvents, and heavy metals), the threshold dosage amount of any SAPH material used in any ingestible form will need to be calculated based upon the regulated residual component found to be closest to its specific threshold maximum daily exposure limit. Accordingly, the maximum acceptable amounts that can be ingested will necessarily be different based upon the specific regulations imposed on each impurity in each country as regulated by such country's governing authority. These rules and regulations change from time to time as new scientific, toxicological, epidemiological and environmental information is developed; and a consensus for setting appropriate exposure limitations is achieved. Therefore, those of skill in the art will recognize that amount of SAPH to be included in any dosage or delivery form may vary. However, those skilled in the art will appreciate the methods needed to be employed to manufacture deliverable goods in each and all of the preferred embodiments herein that will be in compliance with each of these regulations for the disclosed purposes of the present invention. Basically, two preferred delivery means exist for the ingestible SAPH of the present invention; a) Non-combination forms and b) Combination forms.

I. Exemplary Non-Combination Ingestible Forms:

The SAPH compositions of the invention are capable of being delivered in no-combination forms of the SAPH in filled capsules or gelcaps. The SAPH compositions of the invention are safely, conveniently, and cost-effectively provided in such forms.

Using chewable tablets, powders or lozenges is contraindicated with the present invention for three reasons: First, since such delivery forms would potentially or deliberately expose the SAPH of the present invention to the salivary amylase and other degradation and digestive materials located in the saliva of the mouth that act to prematurely reduce the swelling ratio of the SAPH (prior to concomitant exposure and activation by the co-ingested free water), the SAPH's bulking capacity in the stomach is reduced. Second, the SAPH of the present invention has no taste whatsoever; and if tasted directly without the addition or presence of flavoring agents or other modifiers as may be otherwise provided in combination and along with other more palatable ingredients as are known by those skilled in the art, such taste establishes a disturbingly unpleasant sensation of poor palatability which reduces the user-friendliness and therefore the user-compliance of the product. Third, the manufacture of tablets and lozenges involves high compression methods that: a) may require the addition of incompatible ingredients (pH, chemical instability or reactivity, etc.) used for tableting that reduce the effectiveness of the SAPH, and b) can induce non-homogenous heating to the material being compressed. If such compression methods heat any of crystalline domains of the SAPH beyond the glass transition point, the SAPH domains so heated would be rendered functionally useless and will reduce the efficiency of the material according to the principles and specific purposes of this invention.

The maximum single unit dose of the SAPH of the present invention provided in convenient capsule or gel cap form would be delivered in '000' capsules sizes, which is the largest standard commercially available capsule size. The milligram amount of the SAPH of the present invention that can be contained in a '000' capsule is dependent upon the apparent bulk density of the SAPH of the present invention. The apparent bulk density is governed by the average particle size of the final material which can be modified as desired based on industry standard methods of comminution and serial mesh sieving methods as described herein. As an example, but not intended to be limiting, an SAPH of the present invention with an apparent bulk density of 0.8 g/cc would provide approximately 1.0 g of SAPH in a '000' capsule. Taken as recommended as one or two capsules consumed with 6 to 12 oz of water per capsule 30 to 60 minutes before meals, the maximum daily exposure of a person to the SAPH of the present invention would be calculated as 6 g per day. More preferably in the non-combination form, the SAPH of the present invention is provided in '00' size capsules containing 750 mg of SAPH with an apparent bulk density of 0.8 g/cc, thus delivering a maximum daily exposure of 4.5 g per day when taken as directed. Therefore, preferred dosage forms of both Non-Combination and Combination forms of the present invention in smaller amounts would contain even fewer contaminants than the most concentrated form.

The hard capsule shells of the preferred embodiment are made from hard gelatin which is certified BSE-free and meets kosher standards; with fast-dissolving hard shells being most preferred. The more preferred embodiment uses vegetable shells, otherwise known by a variety of commercial names with one example being "Veggie Caps" as such are provided by Capsuline® Inc., and other suppliers. The most preferred embodiment of the present invention when delivered as a non-combination product is in the form of gel caps. Other dosage sizes can be easily prepared by altering the apparent bulk density, adding excipients, or using different size capsules or gel caps by incorporating standard methods well known in the art.

As will be recognized by those skilled in the art, the concept of non-combination forms, as used by the applicant in the context of the disclosure of the present invention, would not exclude the incorporation of small quantities of antimicrobial preservative agents, such as methylparaben and or propylparaben. These preservatives are commonly used in pharmaceutical and food products, and the addition of small quantities of the preservatives does not interfere with the principles, practices and purposes of the present invention. When present, these preservatives can be added to the SAPH material of the present invention in an amount typically less than 0.5% by weight, based on the total weight of resinous crystals in the mixture.

Furthermore, capsules or gel caps filled with the SAPH of the present invention using standard capsule filling methods contain numerous voids among the SAPH particles which can be filled in with finely ground powders of numerous desirable compositions. Examples of such compositions could include but without limitation; flavorings, active ingredients, nutritional ingredients, natural products, pharmaceutical products, excipients, adjuvants, inert materials or other compositions of matter that would modify, augment or otherwise enhance the commercial appeal of the product, broaden its usefulness, or provide some additional, expanded or alternative benefit to a stand-alone SAM material of the present invention. In addition, the compositions may optionally include additional edible non-toxic ingredients as conventionally employed in medicinal dosage forms. Thus, the compositions of the invention may optionally include one or more excipients in an amount within the range of from about 0.1% to about 99% by weight, examples of such, which are not intended to be limiting include: lactose, sugar, corn starch, modified corn starch, mannitol, sorbitol, and inorganic salts such as calcium carbonate and others. Other conventional ingredients which may optionally be present include flavorings, preservatives, stabilizers, plasticizers, anti-adherents or silica flow conditioners or glidants, such as Syloid brand silicon dioxide as well as FD&C colors.

Furthermore, the present invention provided in the non-combination form of capsules or gel caps can be delivered in numerous unit dose or multi-dose packagings well known in the art, included but without limitation: a) bottles; b) blister-packs; c) foil pouches; d) packets; and other common packaging forms common to the sale of capsules or gel caps. In addition, the present invention would carry a label and or a package insert with all pertinent information as may be regulatorily mandated and or as may otherwise be commercially desirable. Additional packagings are envisioned and are not intended to be limited by this disclosure.

Clinical Data Validation:

An exemplary embodiment of a SAPH of the present invention was clinically evaluated in its non-combination form in a prospective, multi-site physician-directed open-label study of 100 patients. The study was entitled "Use of a New Synthetic Gastric Bulking Agent for Weight Management." The object of the 4-week study was to clinically test the utility of the present invention for use as a temporary pre-meal gastric bulking agent designed to maximally suppress appetite thus assisting in reducing appetite, reducing meal portions and subsequently in assisting in weight management. The study's inclusionary criteria were: a) Participants wishing to manage their weight; b) Age Range: 18-75, and c) Participants who signed the Informed Consent Form, and the Model Release Form. The exclusionary criteria were: a) Participants who were non-compliant with testing or questionnaire regimens; b) Participants who were unable to tolerate taking the SAPH of the present invention the in Non-Combination form of 750 mg hard shell capsules; c) Participants under 18 or over the age of 75; d) Participants with moderately severe co-morbid disease, that includes cardiac, pulmonary, renal, gastro-intestinal, hepatic, or active cancer (this determination is subject to the study nurse and/or physician), or a history of GI surgery, and e) Participants with alcohol or drug abuse as determined by provider interviews or medical history.

Participants were placed on a diet and exercise program in addition to protocol ingestion of the present invention. Information was collected weekly for four weeks from each person regarding: a) certain personal information; b) diet and eating habits and behaviors; c) SAPH utilization; d) SAPH effectiveness; e) hunger status; f) meal portion sizes, and g) any associated side effects or adverse events. The SAPH composition of the invention that was utilized in the clinical trial is currently being sold under the tradename, PREE™. The recommended diet included a very-low amount of refined carbohydrates; although the overall plan included equal amounts of total carbohydrates, fats, and proteins. The recommended use of carbohydrates involved the use of complex carbohydrates, mostly green vegetables and grains, such as brown rice, with a repeated emphasis on extremely small amounts of refined carbohydrates, including soda, products containing sugar, corn syrup, wheat products, breads, pasta, potatoes, and similar foods. Each subject was counseled about these diet concepts throughout the study and again at the weekly check-in periods. Furthermore, participants were asked to comply with a moderate exercise program.

Protocol:

1. Participants were recruited from those who were actively seeking medically supervised weight-loss.
2. Participants met the inclusionary and exclusionary criteria and passed a health-screening provided by the clinic.
3. Participants received pre and post study photos.
4. Participants were terminated from the study without prejudice if they repeatedly failed the compliance standards involving dosing, diet, exercise or failure to complete the study questionnaire.
5. Participants were required to sign the Informed Consent, indicating that they understood all aspects of this trial; and Model Release Form allowing use of their pictures.
6. The Study Coordinator instructed all Participants as to the protocol and other details of the study.
7. Participants were instructed precisely as to how and when to take the present invention during the course of this study and how to report adverse reactions and any other pertinent information.
8. Participants were given a study folder containing the instructions, 4 Questionnaires, and a one-month supply of present invention (bottle containing 90 capsules containing 750 mg of the SAPH of the present invention).
9. Participants were screened into the study by a physician or staff nurse.
10. Participants received instructions on how and when to complete the questionnaire and where to fax the document weekly.

11. Participants were required to come back to the clinic every week for four weeks to have their blood pressure, weight, body composition checked and complete the Questionnaire; and to obtain pre and post study photos.

12. Any adverse events were reported to the clinic or supervising physician immediately.

The study's two primary endpoints were: a) safety as documented by the listing and rating of any and all side effects and related adverse events; and b) the ability of the present invention to control appetite. The Study's two secondary endpoints were: a) the ability of the present invention to reduce meal portions consumed; and b) the degree of weight change over the course of the study. The SAPH was provided in the form of 750 mg SAPH in 2-piece gelatin capsules. Patients were instructed to take one to two capsules 30 to 60 minutes before each meal with 6 to 12 oz of water per capsule. Patients were provided with 90 capsules and a study packet with a questionnaire to be filled out at baseline then weekly for four weeks. The data was collected and analyzed independently.

Analytical Methods:
1. Answers from the Questionnaire tools were coded from 1 to 5
2. Answers from the Questionnaires were subtracted from each Participants' baseline data to create the outcome measures
3. The responses for each question were analyzed using a t-test, Chi-Square test, Fisher's Exact Two-Tail t-test, or an ANOVA analysis where appropriate.

Categorical Analysis:
One-point differences were classified as "Minimal Improvement", two-point differences as "Mild Improvement", three-point differences as "Significant Improvement", four-point differences as "Dramatic Improvement", and five-point differences as "Maximal Improvement". All categories were analyzed using the Chi-Square test.

Statistical Significance:
Statistical significance ratings were: a) Highly Significant: $p<0.05$; b) Significant: $p<0.10$, and c) Statistical Trend: $p<0.15$ Preliminary Results:
Results from the study's first 24 participants with 2 weeks of information as analyzed and reported below:
1. Responders: 95.8% (23/24)
2. Average Reduction in Portion Size: 21.0%
3. Average Rating of Hunger Control Effectiveness: 88.9%
4. Average Time to "feel" Fullness Effect: 36 minutes
5. Average Duration of Effect: 2.1 hours
6. Average Weight Loss: 4.6 pounds over the initial 2 week period
7. Doses Administered: >1500
8. Side-effects or Adverse Events Reported:
  1. 4 patients with mild burping
  2. 2 patients with mild constipation
  3. 1 patient with moderate cramping sensation
  4. 1 patient with mild chills
  5. 1 patient with a mild headache Final results and statistical analyses will be tabulated, statistically analyzed and included in the final patent application.

Figure 2:
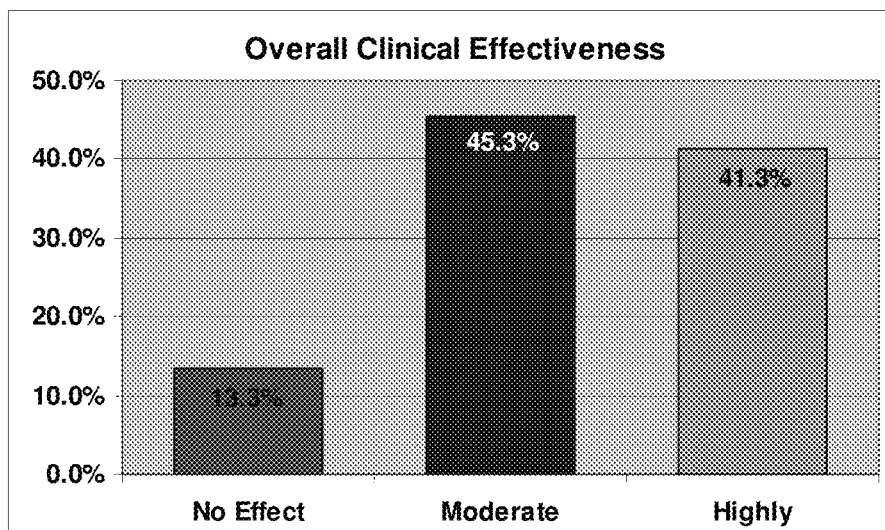
FIG. 2. Graphical representation of clinical trial data relating to participant response to ingestion of an exemplary SAPH composition of the invention (commercially available as PREE™). Participants were asked to provide an overall combined score for PREE™, in terms of its ability to reduce meal portions and control hunger at each of the three meals daily, combined with an ability to translate these feelings into weight loss. Based on these criteria, participants rated PREE™ as: a) Not Effective: 13.3% of the time; b) Moderately Effective: 45.3% of the time; and c) Highly Effective: 41.3% of the time.

The findings are summarized below, with reference to FIGS. 1-5:
1. Participant Statistics:
  Average Age: 49
  Average Beginning: BMI—30.5; Weight—183 lbs; Height—65 in
  Average Ending: BMI—29.3; Weight—175 lbs; Height—65 in
2. Responders: 94.1%
3. Average 4-week Weight Loss: 7.6 lbs (4.2% of Body Mass)
4. Average Number of Capsules Taken per Day: 2.1
5. Average Reduction in Meal Portion Size: 34.3%
6. Average Rating of Hunger Control Effectiveness: 86.7%
7. Average Time to "feel" Fullness Effect: 33 minutes
8. Average Duration of "Fullness" Effect: 2.5 hours
9. Total Doses Administered: >2,000
10. Total Incidence of Side-effects: 3.6%; Adverse Events: None Clinical trial participants were asked to rate their responses from PREE's effects at each of breakfast, lunch and dinner (FIG. 1). PREE™ generated a sensation of fullness or early satiety 94.1% of the time. In 5.9% of meals, patients described that "No Effect" was noted. In addition to simply feeling a sense of fullness or early satiety with meals, participants were asked to provide an overall combined score for PREE™ in terms of its ability to reduce meal portions and control hunger at each of the three meals daily, combined with an ability to translate these feelings into weight loss (FIG. 2).

Figure 3:
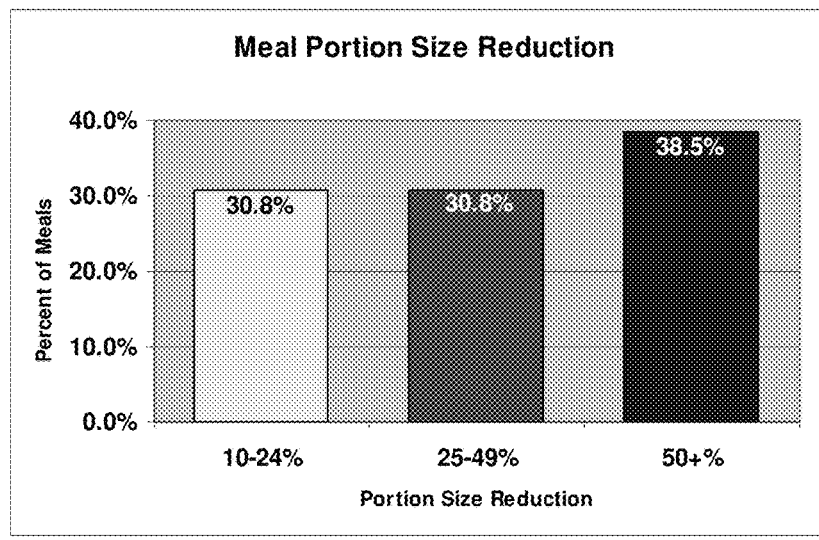
FIG. 3. Graphical representation of clinical trial data relating to participant response to ingestion of an exemplary SAPH composition of the invention (commercially available as PREE™). Responding participants were asked to gauge the degree of their meal portion reduction in terms of the percentage decrease from their regular meal sizes.

Of the 94.1% of participants that experienced a clinical effect from PREE™ (see Graph 1) it was important to understand not only if an effect was felt from PREE™ but whether or not that effect actually caused meal portions to be reduced; and if so, by how much. Responding participants were asked to gauge the degree of their meal portion reduction in terms of the percentage decrease from their regular meal sizes (FIG. 3). As shown in FIG. 3, 30.8% of the time meal portions were reduced by 10-24%. Equally, 30.8% of the time meal portions were reduced by 25-49%, with portion sizes reduced by 50% or more 38.5% of the time. The average meal portion reduction as reported in this study was 34.3%.

Figure 4:
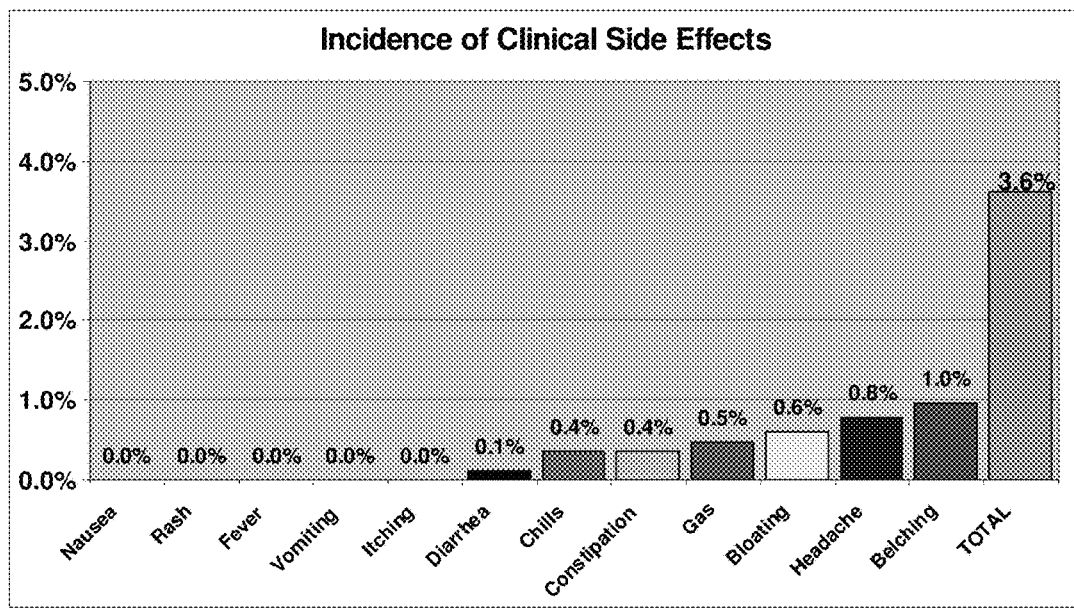
FIG. 4. Graphical representation of clinical trial data relating to participant response to ingestion of an exemplary SAPH composition of the invention (commercially available as PREE™). The incidence of occurrence of all study related side effects was recorded.

One of the most important findings of this or any clinical study is the determination of side effects and the recording of any study-related adverse events. FIG. 4 shows the incidence of occurrence of all study related side effects. Of importance, no adverse events were reported during the study. Participants were also asked to report all side effects that they could relate to taking PREE™. A total of 3.6% of meals were accompanied with some form of side effect. Participants were asked to rate the effects on a five point scale ranging from 1 (no effect) to 5 (very severe). One person reported bloating rated at a "4" when taking 2 capsules 3 times daily before meals. No other side effects were rated higher than 3 (moderate). Slight belching for a few minutes as the capsules dissolved (within 10 minutes of ingestion) was the most common side effect reported. Occasionally, these burps were accompanied with an unpleasant taste rated no more than 2 (mild).

Figure 5:
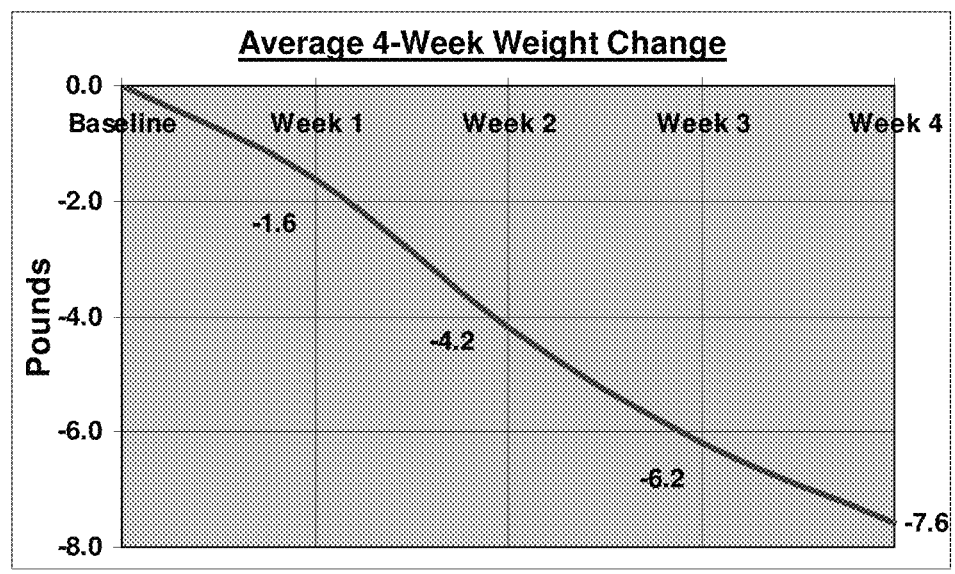
FIG. 5. Graphical representation of clinical trial data relating to participant response to ingestion of an exemplary SAPH composition of the invention (commercially available as PREE™). The ability of PREE™ to assist participants in losing weight was measured.

The ability for PREE™ to assist participants in losing weight was also measured. As can be seen in FIG. 5, participants lost an average of 1.9 pounds per week, with an average weight loss of 7.6 pounds over the 4-week study. Most weight management experts agree that if weight is lost too rapidly it will generally not be sustainable. Therefore, most recommend that people lose weight more slowly—generally in the range of 1 to 2 pounds per week so that the weight that comes off can stay off.

The SAPH compositions of the invention are designed and efficacious for helping individuals lose weight sensibly and progressively without feeling hungry or deprived in the process.

II. Exemplary Combination Ingestible Forms:

The SAPH of the present invention is highly adaptable and can be flexibly, multiply and alternatively incorporated into numerous useful ingestible forms when combined with other ingestible materials, components and ingredients. The specific purpose which combines the SAPH of the present invention with other ingestible materials would be to provide a weight loss and or weight management dimension to the other material(s) incorporated into the ingestible form which they alone would otherwise lack or alternatively not maximally provide a hunger suppression capability.

As will be appreciated by those skilled in the art, the SAPH of the present invention is a resinous material that exhibits an increasingly granular texture with increasing particle size. One primary object of the present invention, which can be optionally incorporated into combination forms, will be to mitigate the granularity of larger sized particles of the material by a softening means. Such means will preferably occur through the use of a final hydrating step whereby the resinous SAPH material form can be quickly washed, sprayed or misted by an aqueous solution, which is preferably comprised of tap water and more preferably by distilled water, and most preferably by flavored water, very briefly to soften the material, but in far less time than to allow for any substantial degree of swelling. The contact time of the SAPH will range from 1 second to 1 minute, depending on the original particle size selected and the degree of softening desired. Of note, those skilled in the art will recognize that the softening occurs at the expense of the swelling ratio, which will need to be accounted for in the final delivery form. More preferably the dry resin can be mixed or tumbled in an aqueous mist of precisely measured amount of water with vigorous mixing to ensure contact all of the particles with the water content and to allow a controlled amount of softening. Most preferably at the completion of the drying step, the temperature will be lowered to 30° C. as the nitrogen atmosphere is replaced with humidified air and admixed with the SAPH material until softening occurs. The timing for the air mixing will preferably range from 1 second to 3 minutes, more preferably from 3 minutes to 1 minute, and most preferably less than 1 minute depending upon the average particle size and the desired degree of softening. The thus softened resinous SAPH of the present invention can then be incorporated into various applications, for example mixes, food bases and many other final forms, some further examples are listed below, and some of which are more responsive to the needs of a softened SAPH, most assuredly in those applications where the SAPH is exposed to the mastication actions of the mouth and is subsequently ingested. Such forms would include by example, but not limited to: cookies, baked goods, certain confectionaries, pressed bars, and other similar delivery means as are well known by those skilled in the art where a granular texture of unsoftened material would be commercially undesirable.

In order to further illustrate the adaptability of the SAPH of the present invention as a combination ingestible form as well as the advantages thereof, the following more specific examples are given. These examples describe a number of such uses as such are anticipated by the applicant and can be anticipated by those skilled in the art. The examples are not intended to be a complete list. The examples are intended to be illustrative only of the principles and practices of this invention and are therefore not intended and are understood to in no way limit the scope of the present invention as can be interpreted by the meanings disclosed herein.

Example III: SAPH Composition

Capsules or gel caps filled with the SAPH of the present invention using standard capsule filling methods contain numerous voids among the SAPH particles which can be filled in with finely ground powders of numerous desirable compositions. Examples of such compositions could include but without limitation; flavorings, active ingredients, nutritional ingredients, natural products, pharmaceutical products, excipients, adjuvants, inert materials or other compositions of matter that would modify, augment or otherwise enhance the commercial appeal of the product, broaden its usefulness, or provide some additional, expanded or alternative benefit to a stand-alone SAPH material of the present invention. In addition, the compositions may optionally include additional edible non-toxic ingredients as conventionally employed in medicinal dosage forms. Thus, the compositions of the invention may optionally include one or more excipients in an amount within the range of from about 0.1% to about 99% by weight, examples of such, which are not intended to be limiting include: lactose, sugar, corn starch, modified corn starch, mannitol, sorbitol, and inorganic salts such as calcium carbonate and others. Other conventional ingredients which may optionally be present include flavorings, preservatives, stabilizers, plasticizers, anti-adherents or silica flow conditioners or glidants, such as Syloid brand silicon dioxide as well as FD&C colors.

Quite unexpectedly, during Applicant's experimentation with numerous filling agents for encapsulation, a novel reaction that has never been described was observed through the mixing of a unique combination of what was previously believed to be inert ingredients. When the SAPH of Example I or II is mixed with stearic acid, magnesium stearate and talc, the resultant mixture imparts a substantial improvement in water-swelling characteristics to the SAPH that was heretofore unknown and undescribed. The combination mixture demonstrates a substantial increase in final particle size by 10% to 100% with improved turgor, color, buffering and other physical and chemical characteristics desirable of an ingestible SAPH designed for use as a gastric bulking agent. Furthermore, the addition of these ingredients improves the flowability of the SAPH material for ease of capsule filling at reduced costs.

In an exemplary embodiment, the SAPH mixture comprises from about 50% to about 99% by weight of SAPH. In certain embodiment the SAPH mixture comprises at least about 80.00%; at least about 90.00%; or about 92.59% by weight of SAPH.

In another exemplary embodiment, the SAPH mixture also comprises from about 0.01% to about 20.00% by weight of stearic acid. In certain embodiments the SAPH mixture comprises at least about 0.10%; at least about 1.00%; or at least about 2.78% by weight of stearic acid.

In still another exemplary embodiment, the SAPH mixture also comprises from about 0.01% to about 10.00% by weight of magnesium stearate. In certain embodiments the SAPH mixture comprises at least about 0.10%; at least about 1.00%; or about 1.85% by weight of magnesium stearate.

In another exemplary embodiment, the SAPH mixture also comprises from about 0.01% to about 20.00% by weight of talc. In certain embodiments the SAPH mixture comprises at least about 0.01%; at least about 1.00%; or at least about 2.78% by weight of talc.

In a preferred embodiment, the ratio of the three excipient ingredients in the SAPH mixture is 3:2:3 parts of stearic acid, magnesium stearate and talc respectively. Without being limited to any particular theory, it is hypothesized that the particular ratio of ingredients directly affects the swell-properties of the mixture. However, because the invention relates to an unpredictable art, the synergistic interaction of the ingredients could not have been predicted.

The excipient materials of the present invention are blended together sequentially in a standard pharmaceutical mixer with a method well known to those skilled in the art. The mixing is accomplished in two stages. The first preblend is comprised of the SAPH mixed together with the stearic acid and magnesium stearate. The talc is added into the mixture as a second preblend and the resultant combination of all four ingredients is mixed until it is homogenous ranging from about 2 to about 20 minutes. The mixing is performed at room temperature and pressure under dehumidified air.

In addition to the usefulness of the SAPH mixture in a non-combination capsular form, the SAPH mixture of the present invention can be effectively used in any of the other forms described herein. By premixing the ingredients as described above, then adding the SAPH mixture to nutritional bars, dietary supplement mixtures, foods, and numerous other applications as would be readily appreciated by those skilled in the art, users can maximize the water-swelling characteristics of the SAPH as desirable for these ingestible applications. In addition to the improved flowability and cost, the mixture improves palatability, texture and flavor of the final ingestible product as well.

Crystalline excipients like those described herein are known to those of skill in the art. Although stearic acid has been used as a process control agent in the blending of metals, in its dry-powder crystalline forms, stearic acid or its magnesium salt are not known to interact with talc, and certainly their particle interactions have not been previously described with any materials like the SAPH of the previously described invention. This synergistic ability to enhance the water-swellable characteristics of the SAPH in this instance is unprecedented, and currently remains unexplained from a dry chemistry perspective. See, Influence of stearic acid on mechanochemical reaction between Ti and BN powders; Jung-Soo Byun, Jae-Hyeok Shim and Young Whan Cho. Nano-Materials Research Center, Korea Institute of Science and Technology, Seoul 136-791, South Korea, which is incorporated herein by reference for all purposes.

1. Dietary Supplements.

Dietary supplements, as such are regulated in the United States by the US Food and Drug Administration (FDA) and similar bodies internationally, are typically orally delivered forms that can contain numerous permutations and combinations of components selected from a variety of classes of active and or inactive ingredients including, but not limited to: a) vitamins; b) minerals; c) herbs; d) extracts; e) probiotics; f) pro-hormones; g) enzymes; h) amino acids; i) proteins; j) lipids; k) carbohydrates; l) botanical, flower, root and or other natural animal and plant products and derivatives; m) oils; n) seeds; o) fruits; p) excipients; q) adjuvants, r) flavorings; s) stabilizers; t) preservatives, u) spices; v) anti-oxidants, w) pH buffers, x) excipients; y) adjuvants, and numerous of other types and classifications of materials, and ingredients as are well known by those skilled in the art.

The SAPH of the present invention can be supplied in combination with each one or in any combination of these abovementioned materials and ingredients. Preferably, the SAPH of the present invention being combined in capsule or gel cap form will vary from 0.01% to 99.99% SAPH weight percent, depending on the desired requirements of the final product combination. Particle size of the SAPH can also be modulated as required.

Some of the specific use applications for these dietary supplements would provide combinations of ingredients specifically formulated for: a) energy and metabolism; b) anti-aging; c) memory; d) athletic performance and endurance; e) hair, skin and nail formulas; f) vision and eye formulas; g) bone and joint formulas; h) prostate formulas; i) erectile dysfunction; j) sleep; k) anxiety; l) women's health formulas; m) heart and circulation formulas; n) cold and flu formulas; o) general wellbeing, and dozens of other remedies in formulations that would contain components that are well known to those skilled in the art.

It is one of the primary objects of the present invention to combine the SAPH of the present invention with these traditional nutritional supplement ingredients to form the first specialty product line of dietary supplements designed specifically for and commercially targeting the weight loss/weight management market. The objective of this novel combination product line will be to provide commercially reasonable solutions for people who not only want nutritional supplementation, but also want to simultaneously lose or manage their weight; but most preferably want to use a SAPH material to provide temporary pre-meal gastric bulking as a means to mediate their appetite and manage their residual hunger in order to comfortably reduce their caloric intake by decreasing their portion size.

Finally, due to the polyelectrolyte structure of the SAPH of the present invention, stability studies need to be completed for each combination to determine shelf life labeling prior to commercialization. If any interactions occur among the ingredients and the SAPH of the present invention that reduce the shelf life to less than a commercially reasonably threshold, various techniques that are well known in the art can be applied to isolate the ingredients while combinationally encapsulated on the shelf awaiting consumption. Such techniques that extend the useful shelf life to commercially reasonable limits include but are not limited to: coatings, microencapsulation, lipidation, partitioning, and others.

2. Meal Substitutes and Food Additives:

Commercially available meal substitutes are currently sold in many forms including: powders, puddings, cookies, shakes, or bars just to name a few. The SAPH of the present invention can be numerously incorporated into each category of meal substitute, quickly, easily and cost-effectively so long as the follow-on processing steps do not involve heating the material above the glass transition temperature of the SAPH which is 102.degree. C. —for the present invention. Furthermore, as a business methodology, the SAPH of the present invention could be supplied as in Example 1 above as a co-sale item to be purchased along with, in combination with, attached with, packaged with, or otherwise sold in a related fashion with the Meal Substitutes.

When commercially provided in the form of a powder, the SAPH of the present invention is most preferably formulated with anhydrous colorants, sweeteners and flavorings that combine to make an attractive and tasteful ingestible treat when mixed with water. The water can be hot (as in cinnamon-apple flavored mixes, cocoa flavored mixes), or cold as desired. When the SAPH mixture is added to water, the SAPH material rapidly absorbs the water to form a gel material which can be both fun to make and pleasurable to eat. This would be especially important for uses envisioned with children. The consistency of the final product can be varied according to the average particle size of the SAPH used and the relative amount of water added. Drinks and shakes are made by adding ultra-fine resinous SAPH crystals in the mix into an excess of water. The more water that is added produces a proportionally thinner resulting drink. Larger grain SAPH in slightly less water will produce a consistency ranging from thin mucilage to a thick pudding-like material which can be individually determined by the user. The resultant mixture can be consumed at room temperature or the mixture can be subsequently chilled or heated to the point of boiling water as desired, so that the material will develop consistencies ranging from gelatin to tapioca pudding—only the mixture will not have the calorie content typically associated with similarly-used commercially available products. Obviously, from Example 1 above, numerous nutritional, natural products, supplement ingredients and other additives can be included as desired to provide a low-calorie, good tasting and nutritious meal substitute at a low cost that is fun and easy to make that has all of the advantages of the resent invention.

The SAPH of the present invention absorbs approximately 500 times g/g its weight in typical city tap water. Therefore, only small quantities of the material will need to be used to make many of the meal substitutes as described herein. A further advantage of this embodiment is the compact size, light weight and end-product volume of such mixtures; which would be extremely beneficial for use by hikers, campers, climbers and recreationists; as well as in certain military expeditionary and special forces applications for inclusion as for example in compact packed rations that could contain energy formulas among others.

3. Dietary Confectionaries and Candies:

The SAPH of the present invention can be incorporated into confectionary and candies of all types and descriptions. Consumed with water, the resultant gastric bulking would reduce appetite thus limiting the desire to over consume these energy-dense, calorie-rich foods. Furthermore, as a business methodology, the SAPH of the present invention could be supplied as in Example 1 above as a co-sale item to be purchased along with, in combination with, attached with, packaged with, or otherwise sold in a related fashion with the Dietary Confectionaries and Candies.

4. Meal Plans:

Commercially available meal plans provide consumers with balanced nutritional and calorie restricted foods. The problem with these plans remains hunger after consumption. The SAPH of the present invention could be incorporated into the substance of the prepared meals in those dishes that did not require heating beyond 100° C. Alternately, as a business methodology, the SAPH of the present invention could be supplied as in Example 1 above as a co-sale item to be purchased along with, in combination with, attached with, packaged with, or otherwise sold in a related fashion with the Meal Plans.

5. Cookies and Other Baked Goods:

Commercially available cookies and other baked goods frequently are dusted with sugar-sprinkles or other toppings after the baking process. Similarly, the SAPH of the present invention can be applied to such baked goods after the heating cycle to promote early satiety and reduce the urge to over-consume these items. Furthermore, as a business methodology, the SAPH of the present invention could be supplied as in Example 1 above as a co-sale item to be purchased along with, in combination with, attached with, packaged with, or otherwise sold in a related fashion with the Cookies and other Baked Goods.

6. Nutrition ("Power") Bars:

Commercially available nutrition bars, as such term is well understood by those skilled in the art, are typically lightly compressed assemblies consisting of recipes of whole foods, grains, fruits, nuts, honey, flavorings, sweeteners, vitamins, minerals and numerous other ingredients well known to those skilled in the art. Typically, these bars are not heated and therefore provide a convenient delivery means for incorporating the SAPH of the present invention directly into the pre-compressed mix. Alternatively, as in Example 5 above, the SAPH of the present invention could be applied to the surface of the bars after fabrication. The average particle size could be varied to provide numerous appearances, consistencies and granularity to meet a wide range of specifications. Furthermore, as a business methodology, the SAPH of the present invention could be supplied as in Example 1 above as a co-sale item to be purchased along with, in combination with, attached with, packaged with, or otherwise sold in a related fashion with the Nutrition Bars.

7. Bottled Water Adjunct:

Despite the controversial findings in a recent study outlining the potential health concerns inherent in drinking too much water, the prevailing scientific and medical opinion includes recommending the ingestion of eight to ten 8 oz glasses of water per day for the average person. Per-capita bottled water consumption has risen almost 50 percent from 2001, to 27.6 gallons in 2006. Globally, the United States is the largest consumer of bottled water, although on a per-capita basis, the US was only $10^{th}$ in 2005. That year, Italians consumed almost twice as much bottled water per capita as Americans. As a result, the bottled water industry is currently posting sales in excess of $11B annually. The diversity of bottled waters is increasing as well. Those skilled in the art will recognize that the reference to bottled water will include any and all suitable predominantly aqueous fluids that would promote the expansion of the SAPH material in the gastric environment which could include but not be limited to: coffee, tea, sodas, juices, flavored waters, activated waters, fortified waters, hydrogen-infused waters, mineral waters, energy and sports drinks, aqueous plant or animal extracts, aqueous biological drinks, carbonated and non-carbonated drinks, and all other forms of bottled or canned liquids with a preponderance of water as the principle ingredient.

Many consumers purchase bottled water for health reasons. Many choose to drink bottled water in combination with weight management programs. Therefore, it is another primary object of the present invention to provide the SAPH of the present invention in capsule or gel cap form as an integral part of the packaging of the bottled water product to provide a convenient means of selling the two items in a value-added single packaging concept. One or more capsules or gel caps can be included in numerous methods.

Preferably, one or more capsules could be conveniently and removably affixed to the external surface of the bottle with tape, a shrink-wrap or other similar means, in a location on the bottle where no shipping damage could occur and potentially incorporating a conspicuous label to draw consumer attention to the presence of the co-packaged SAPH material. More preferably, the capsules or gel caps could be incorporated into the sealing means of times used on the mouth of the bottle beneath the cap. Such a sealing means could contain an easy-peel-off feature common to many such seals and would additionally securably include the capsule or gel cap in a waterproof reservoir means on the undersurface of the seal or more preferrably on the dorsal surface of the seal in a manner such that when peeled off, the capsule or gel cap could be conveniently available for consumption along with the bottled water. Most preferably, the capsule or gel cap could be located in a small compartment that would be integrally located in the cap of the bottled water. The cap could preferably be configured with a living hinge lid, provided as an integrally molded single-piece lid defining a small space where the capsule or gel cap could be contained. More preferably, the lid could be constructed as a snap-on, pop-off feature defining a compartment for the capsule or gel cap beneath. Such snap-on lid would provide for easy automation loading of the capsule or gel cap. Such a lid could also be constructed with a small tab or gripping recess to allow for easy removal by the consumer.

In any event and through the use of any combinatorial packaging means, it is an object of the present invention to include the SAPH of the present invention in an easy, inexpensive manner to be co-located and integrally packaged with a bottled water product. Furthermore, as a business methodology, the SAPH of the present invention could be supplied as a co-sale item to be purchased along with, in combination with, attached with, packaged with, or otherwise sold in a related fashion with the Bottled Water products.

8. Exercise and Fitness Equipment Adjunct:

In addition to other co-sale opportunities, the SAPH of the present invention could be included as a co-sale item with exercise and fitness equipment. The capsules or gel caps could be sold directly with the equipment or alternately advertised simultaneously and offered as an after-purchase sale through discounting means, via Internet continuity sales or other means for example, as such methods are well known by those skilled in the art. Furthermore, as a business methodology, the SAPH of the present invention could be supplied as in Example 1 above as a co-sale item to be purchased along with, in combination with, attached with, packaged with, or otherwise sold in a related fashion with the Exercise and Fitness Equipment.

9. Alcohol Absorbent:

In an unexpected discovery, the SAPH of the present invention has the uncanny capacity to absorb certain common alcoholic beverages, almost to the same extent as pure water. The SAPH of the present invention was tested with numerous commercial brands of beer, wine and bottled spirits. Beer of all brands was well absorbed at swelling ratios of from 250 to 400 times gram for gram. Clear colorless spirits, for example vodka and gin were also well absorbed at 200 to 350 gram for gram—if diluted to less than 10% ethanol as in a glass with sufficient water. Colored spirits, as in various whiskies such as scotch, bourbon and others, were less well absorbed to 100 to 200 times gram for gram, although if diluted sufficiently improved absorption would occur. No absorption occurred with any wines tested; irrespective of whether they were red, white, sparkling or otherwise.

This discovery offers the novel opportunity to provide the SAPH of the present invention to be useful as a sobriety aid means. In addition to other outlets, such a product could be offered in liquor stores, bars and taverns and other locations where alcoholic beverages are sold to assist patrons with moderating consumption, and potentially reducing their blood alcohol levels despite equivalent alcohol volume consumption. As such, the SAPH of the present invention could be commercialized as an adjunctive means to promote more responsible drinking behavior, especially with respect to driving after drinking.

A second benefit of this sobriety aid application would be the early satiety feature of entrapping the alcoholic beverage in the stomach and the subsequent inducement of the sense of fullness, thus limiting the subsequent volume of ingested alcoholic beverage being consumed. Decreases in alcohol consumption would promote a reduction in alcoholism, increase traffic safety, reduce alcohol-related overdoses, and moderate the development of cirrhosis and liver disease. These benefits would substantially reduce the overall societal morbidity, mortality and costs associated with alcohol consumption.

In certain additional embodiments, the invention comprises a method in which the SAPH of the present invention is used (i.e., administered or consumed) over time, to cause the individual to accommodate to reduced sizes of ingested meal portions without feeling residual hunger. Such behavioral modification over time will have many beneficial effects including but not limited to: a) sustainable weight loss; b) reduced food wastage; c) saving money; c) improved self-esteem, and e) reduced health care costs. The use of the present invention to cause a progressive change in perception of the required meal portion size is therefore another primary object of the present invention.

It is understood that the detailed examples and embodiments described herein are given by way of example for illustrative purposes only, and are in no way considered to be limiting to the invention. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present invention will be apparent from the appended claims.

The invention claimed is:

1. A method of modulating appetite in an individual comprising administering an effective amount of a gastric bulking composition for oral delivery in a unitary dosage form prior to a meal, wherein the composition is effective in promoting early satiety and the composition comprises at least one of a crosslinked polycarboxylate homopolymer, a crosslinked polycarboxylate copolymer or combination thereof; and a pharmaceutically acceptable excipient, wherein:

from about 5% by weight to about 20% by weight of the total amount of the composition is retained on a 500 micron mesh;

from about 25% by weight to about 90% by weight of the total amount of the composition is retained on a 180 micron mesh; and from about 1% by weight to about 15% by weight of the total amount of the composition is retained on a 106 micron mesh.

2. The method of claim 1, wherein the polycarboxylate copolymer comprises at least one of an acrylamide, an acrylonitrile, a vinyl pyrrolidone, a vinyl sulphonic acid or a salt thereof, a cellulosic monomer, a modified cellulosic monomer, a polyvinyl alcohol, a starch hydrolyzate, and combinations thereof.

3. The method of claim 1, wherein the composition exhibits a swelling ratio of at least 200 in free water within a gastric environment.

4. The method of claim 1, wherein the composition exhibits a swelling ratio of at least 350 within the gastric environment.

5. The method of claim 1, wherein the composition exhibits a swelling ratio of at least 500 within the gastric environment.

6. The method of claim 1, wherein the polycarboxylate homopolymer or copolymer comprises at least one of an ethylenically unsaturated carboxylic acid, an ethylenically unsaturated carboxylic acid anhydride, or acid or basic salts thereof.

7. The method of claim 1, wherein the crosslinked polycarboxylate homopolymer or copolymer comprises at least one of a polyacrylic acid, a polyacrylamide, or alkali salt thereof.

8. The method of claim 6, wherein the homopolymer comprises a sodium salt of a polyacrylic acid.

9. The method of claim 1, wherein the composition comprises from about 50% to about 99% by weight of a crosslinked polycarboxylate, and from about 1% to about 10% by weight of L-Leucine.

10. The method of claim 9, wherein the composition comprises from about 95% by weight of a crosslinked polycarboxylate, and about 5% by weight of L-Leucine.

\* \* \* \* \*